United States Patent
Chu et al.

(10) Patent No.: US 7,083,595 B2
(45) Date of Patent: Aug. 1, 2006

(54) MEDICAL CATHETER ASSEMBLY AND METHOD OF USING THE SAME

(75) Inventors: Michael S. H. Chu, Brookline, MA (US); Laddvanh Bouphavichith, Clinton, MA (US)

(73) Assignee: Scimed Lipe Systems, Inc., Maple Grove, MN (US)

( * ) Notice: Subject to any disclaimer, the term of this patent is extended or adjusted under 35 U.S.C. 154(b) by 0 days.

(21) Appl. No.: 10/136,110

(22) Filed: May 1, 2002

(65) Prior Publication Data
US 2004/0059293 A1 Mar. 25, 2004

(51) Int. Cl.
*A61M 5/00* (2006.01)
*A61M 25/16* (2006.01)

(52) U.S. Cl. .................. 604/107; 604/95.04; 604/174; 604/533

(58) Field of Classification Search ........... 604/104, 604/105, 109, 171, 174, 264, 95.01, 95.02, 604/95.03, 95.04
See application file for complete search history.

(56) References Cited

U.S. PATENT DOCUMENTS

| | | |
|---|---|---|
| 3,926,187 A | 12/1975 | Iglesias |
| 4,306,545 A | 12/1981 | Ivan et al. |
| 4,390,017 A | 6/1983 | Harrison et al. |
| 4,417,890 A | 11/1983 | Dennehey et al. |
| 4,424,833 A | 1/1984 | Spector et al. |
| 4,473,369 A | 9/1984 | Lueders et al. |
| 4,557,261 A | 12/1985 | Rügheimer |
| 4,774,944 A | 10/1988 | Mischinski |
| 4,826,477 A | 5/1989 | Adams |
| 4,834,712 A | 5/1989 | Quinn et al. |
| 4,861,334 A | 8/1989 | Nawaz |
| 4,863,438 A | 9/1989 | Gauderer et al. |
| 4,944,732 A | 7/1990 | Russo |
| 4,995,868 A * | 2/1991 | Brazier ....................... 604/105 |
| 5,007,900 A | 4/1991 | Picha et al. |
| 5,026,352 A | 6/1991 | Anderson |
| 5,071,405 A | 12/1991 | Piontek et al. |

(Continued)

FOREIGN PATENT DOCUMENTS

EP 976418 2/2000

OTHER PUBLICATIONS

Boston Scientific Corporation sales literature entitled 'Abscess Drainage Products,' published before the filing of the present application.

*Primary Examiner*—Nicholas D. Lucchesi
*Assistant Examiner*—Matthew F. DeSanto
(74) *Attorney, Agent, or Firm*—Kriegsman & Kriegsman

(57) ABSTRACT

A medical catheter assembly and method of using the same. In one embodiment, the assembly comprises a gastrostomy feeding tube having a proximal end, a distal end and a longitudinal bore, the distal end being shaped to include an internal bolster, the internal bolster having an anchoring state and a non-anchoring state. A suture extends from the internal bolster through the longitudinal bore to exit the tube at its proximal end, proximal displacement of the suture maintaining the internal bolster in its anchoring state. A protective sleeve made of a rigid material is removably insertable into the tube through its proximal end, the suture being inserted through the protective sleeve. The protective sleeve, when inserted into the tube, serves to protect the suture from being cut when the tube is cut to a desired length after having been implanted in a patient.

25 Claims, 20 Drawing Sheets

U.S. PATENT DOCUMENTS

| | | | |
|---|---|---|---|
| 5,100,394 A | 3/1992 | Dudar et al. | |
| 5,112,310 A | 5/1992 | Grobe | |
| 5,158,569 A | 10/1992 | Strickland et al. | |
| 5,167,627 A | 12/1992 | Clegg et al. | |
| 5,259,399 A | 11/1993 | Brown | |
| 5,267,983 A | 12/1993 | Oilschlager et al. | |
| 5,290,250 A | 3/1994 | Bommarito | |
| 5,358,488 A | 10/1994 | Surlyapa | |
| 5,399,165 A * | 3/1995 | Paul, Jr. | 604/95.04 |
| 5,454,790 A | 10/1995 | Dubrul | |
| 5,488,949 A | 2/1996 | Kreifels et al. | |
| 5,514,112 A * | 5/1996 | Chu et al. | 604/267 |
| 5,549,657 A | 8/1996 | Stern et al. | |
| 5,720,734 A | 2/1998 | Copenhaver et al. | |
| 5,836,924 A | 11/1998 | Kelliher et al. | |
| 5,928,208 A | 7/1999 | Chu et al. | |
| 5,941,855 A | 8/1999 | Picha et al. | |
| 6,042,577 A * | 3/2000 | Chu et al. | 604/523 |
| 6,095,997 A | 8/2000 | French et al. | |
| 6,231,542 B1 * | 5/2001 | Amos et al. | 604/95.01 |
| 6,364,858 B1 | 4/2002 | Picha | |
| 6,508,789 B1 * | 1/2003 | Sinnott et al. | 604/164.02 |

* cited by examiner

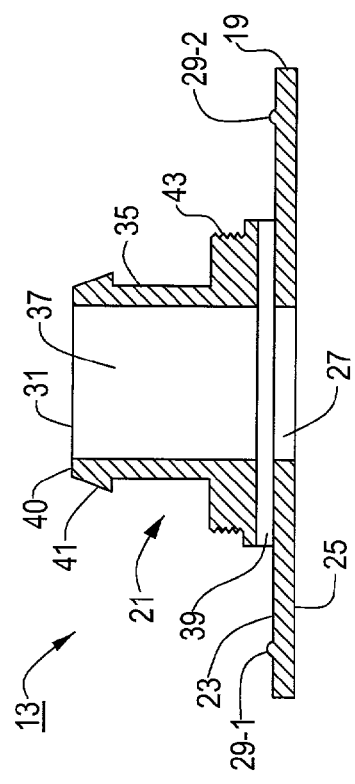
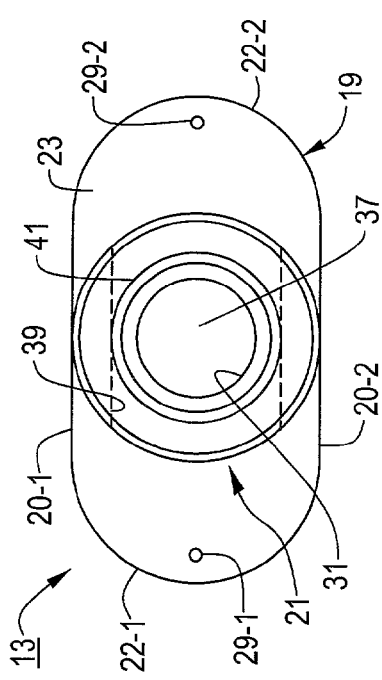
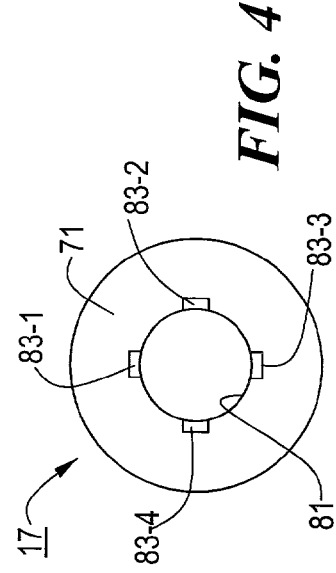
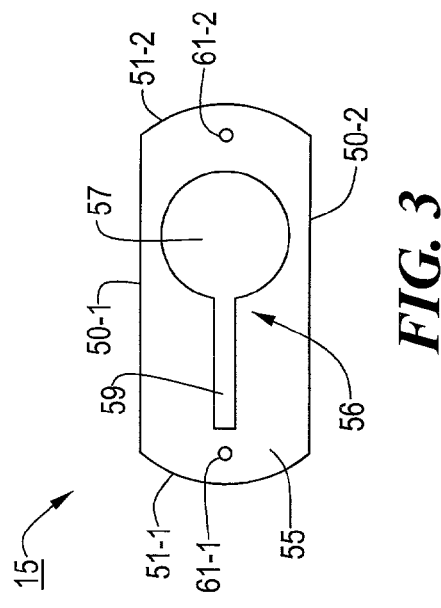

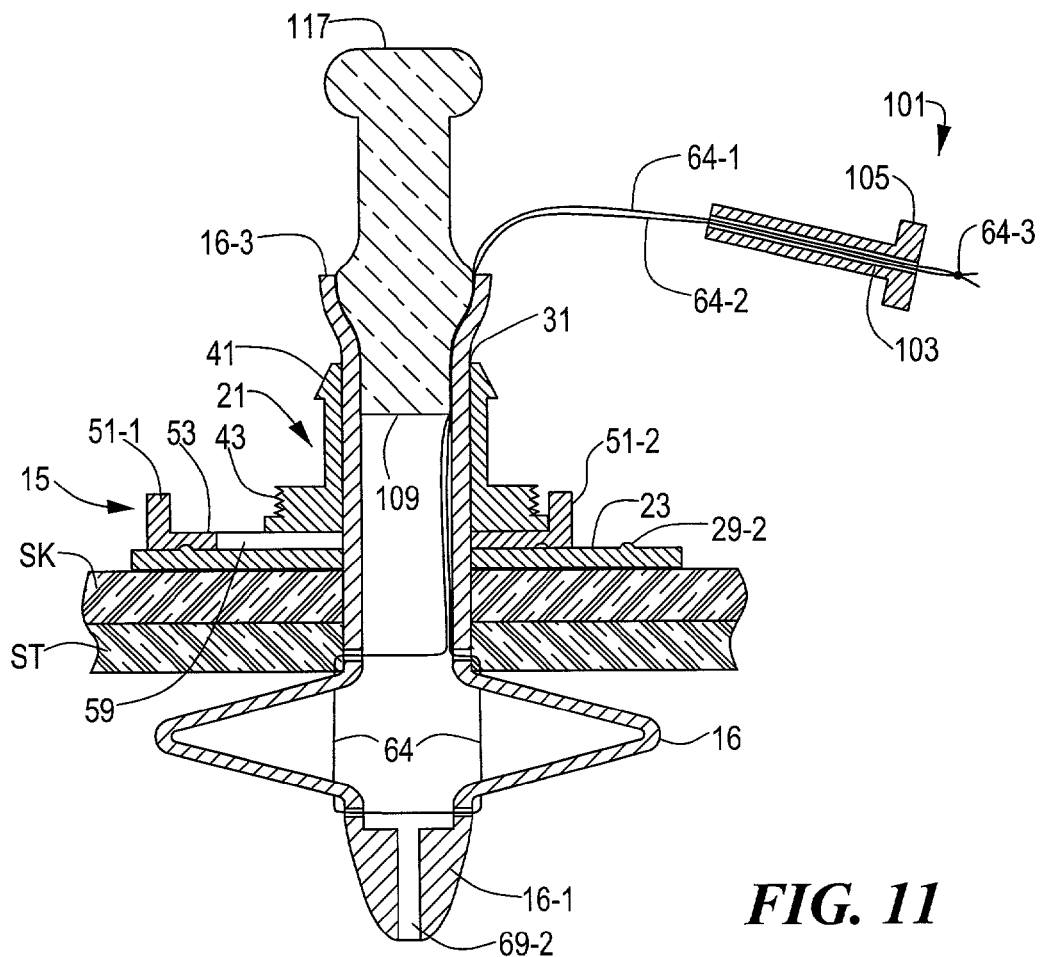
FIG. 11
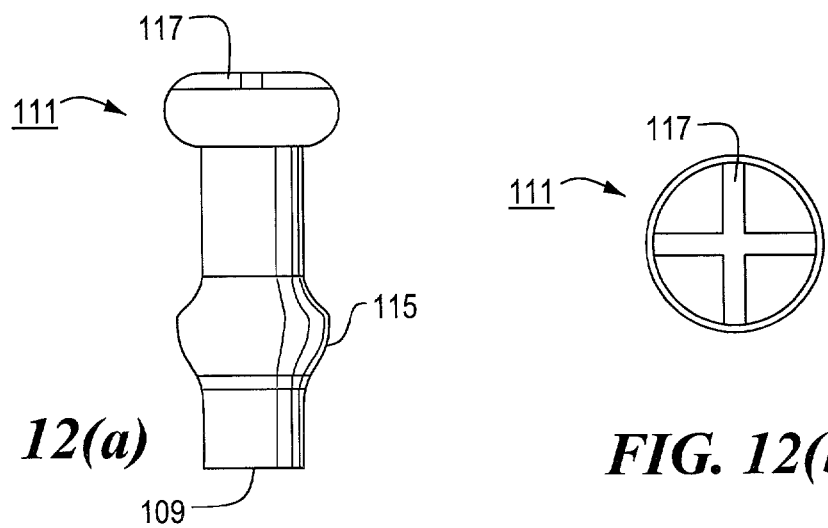
FIG. 12(a)  FIG. 12(b)

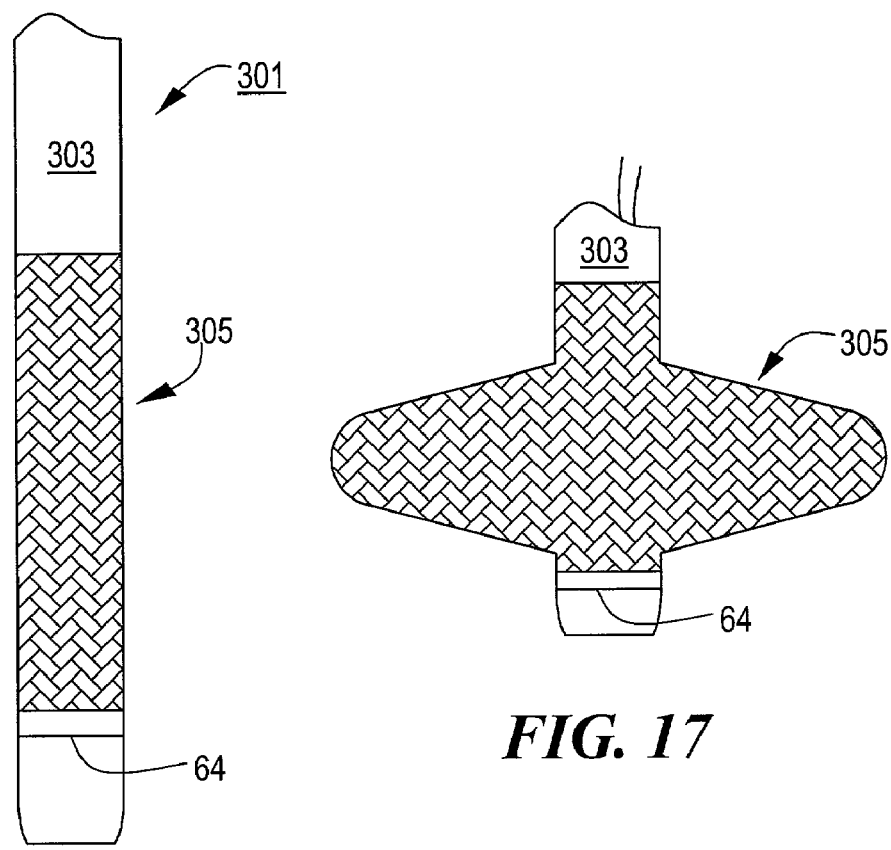
FIG. 17
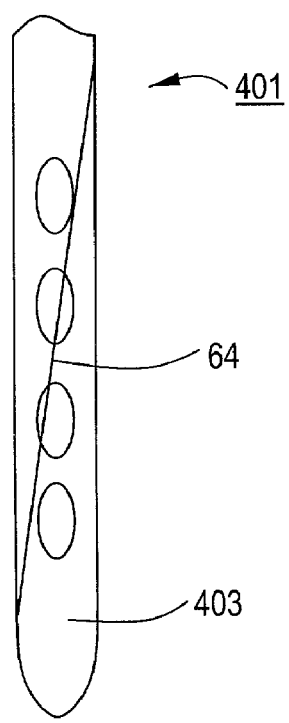
FIG. 16(b)
FIG. 18(b)

MEDICAL CATHETER ASSEMBLY AND METHOD OF USING THE SAME

BACKGROUND OF THE INVENTION

The present invention relates generally to medical catheters, such as gastrostomy feeding tubes, and relates more particularly to medical catheter assemblies, such as percutaneous endoscopic gastrostomy (PEG) devices.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy. In one type of percutaneous endoscopic gastrostomy (PEG) technique, the distal end of an endoscope is inserted into a patient's mouth and is passed through the esophagus into the stomach. After distension of the stomach by inflation, an entry site on the abdomen is identified and an incision can be made. A needle, with an outer cannula, is inserted through the entry site across the abdominal and gastric walls. While keeping the cannula in place, the needle is removed, and a flexible wire is passed through the cannula into the stomach and into a snare loop extended from the distal end of the endoscope. The endoscopic snare loop is then used to grasp the wire, the cannula is released, and the endoscope and wire are withdrawn through the esophagus and mouth of the patient. A silicone gastrostomy feeding tube, the distal end of which is attached to a silicone, dome-shaped internal bolster, is then secured to the wire and is pulled from its proximal end through the esophagus and into the stomach until the internal bolster engages the stomach wall and the feeding tube extends through the stomach and abdominal walls, with the proximal end of the feeding tube extending approximately one foot beyond the abdominal wall. (Over a period of several days following implantation of the feeding tube, a stable stoma tract forms around the feeding tube between the gastric and abdominal walls.)

With the internal bolster in place against the gastric wall, an external bolster is typically secured to the feeding tube to engage the abdomen so as to prevent longitudinal movement of the feeding tube within the stoma tract. Additionally, a "Y-port" adapter is typically attached to the proximal end of the feeding tube, the Y-port adapter being adapted to receive a pair of connector tips through which food and/or medications may be dispensed. In addition, a detachable locking clip is typically secured to the feeding tube at a point between the external bolster and the Y-port adapter to prevent gastric fluids from escaping through the proximal end of the feeding tube when the feeding tube is not in use.

Alternative techniques for implanting gastrostomy feeding tubes using percutaneous endoscopic gastrostomy are disclosed in U.S. Pat. No. 5,112,310, inventor Grobe, which issued May 12, 1992, and U.S. Pat. No. 5,167,627, inventors Clegg et al., which issued Dec. 1, 1992, both of which are incorporated herein by reference.

Although gastrostomy feeding tubes of the type described above work well for their intended purpose, many active patients find the nearly one foot length of tubing that extends externally to be unwieldy, difficult to conceal and susceptible to being inadvertently pulled on. As can readily be appreciated, these conditions are potential sources of physical and/or psychological trauma to the patient. Consequently, a variety of low-profile replacement tube assemblies (also referred to in the art as low-profile replacement PEG devices) have been designed for implantation within the stoma tract following the removal of an initially-implanted gastrostomy feeding tube. Such replacement assemblies are referred to as being "low-profile" because they are considerably more compact externally than the above-described initially-implanted gastrostomy feeding tube assemblies.

An example of a low-profile replacement PEG device is disclosed in U.S. Pat. No. 4,944,732, inventor Russo, which issued Jul. 31, 1990, and which is incorporated herein by reference. The low-profile replacement PEG device of said patent comprises a deformable, conical tip portion having at least one side aperture therethrough, a tube portion which extends rearwardly from the tip portion, a fitting portion on the rear end of the tube portion, a removable valve portion in the fitting portion and a flange portion which extends outwardly from the fitting portion. The device is adapted to be installed in a patient so that the tube portion extends through a pre-established stoma with the tip portion located in the patient's stomach and with the fitting portion and the flange portion engaging the skin of the patient adjacent the stoma.

The deformable tip portion of the above-described low-profile replacement PEG device functions as an internal bolster to anchor its associated tube portion in a patient's stomach. To implant and/or remove the aforementioned tube portion from a patient's stomach, an obturator or similar device is typically inserted through the tube portion and is used to elongate or otherwise deform the tip portion in such a way as to permit the tip portion to fit through the stoma. Removal of the obturator from the tip portion then permits the tip portion to expand to its original shape for anchoring.

Another type of low-profile replacement PEG device uses an inflatable balloon, instead of a deformable tip portion, as an internal bolster to retain the distal end of its associated tube within a patient's stomach. To implant such a device in a patient, the inflatable balloon is deflated, the distal end of the tube portion is inserted through the stoma, and the balloon is then inflated. To remove the implanted device from a patient, the balloon is deflated and the tube is then withdrawn from the stoma.

Further examples of low-profile replacement PEG devices are disclosed in U.S. Pat. No. 4,863,438, inventors Gauderer et al., which issued Sep. 5, 1989; and U.S. Pat. No. 5,720,734, inventors Copenhaver et al., which issued Feb. 24, 1998, both of which are incorporated herein by reference.

Although low-profile replacement PEG devices are less awkward and bulky than initially-implanted gastrostomy tube assemblies, the use of such low-profile replacement PEG devices suffers from its own set of shortcomings. One such shortcoming is that the implantation of a low-profile replacement PEG device must be preceded by the removal of an initially-implanted gastrostomy tube. Such removal typically involves pulling on the proximal end of the gastrostomy tube until the internal bolster fails and is drawn through the stoma. As can readily be appreciated, such a procedure can be quite painful to the patient and can result in damage to the stoma, thereby delaying when the replacement device can be implanted.

Another shortcoming of many low-profile replacement PEG devices is that such devices typically do not last as long as initially-implanted gastrostomy tube assemblies (most commonly due to failure of their internal anchoring mechanisms or due to clogging or other failure of their valve mechanisms) and, therefore, must be replaced more frequently than is the case with initially-implanted gastrostomy tube assemblies.

Still another shortcoming of many low-profile replacement PEG devices is that such devices are typically not adjustable in length. This can be problematic because there is often an appreciable variation in stoma length from patient to patient. Consequently, it is typically necessary, after removal of the initially-implanted tube and prior to implantation of the replacement device, to measure the length of the stoma and then to select a replacement device having an appropriate length. As can readily be appreciated, this approach requires that there be made available an inventory of replacement devices of varying lengths.

In order to avoid the aforementioned shortcomings of low-profile replacement PEG devices while, at the same time, avoiding the above-described problems associated with having a gastrostomy tube extend externally for a substantial length, there have recently been devised a number of adaptors designed for use in converting an initially-implanted gastrostomy tube into a low-profile PEG device. One such adaptor is disclosed in U.S. Pat. No. 5,549,657, inventors Stern et al., which issued Aug. 27, 1996, and which is incorporated herein by reference. According to said patent, an adaptor is disclosed therein that is designed for use with a gastostomy feeding tube which has been inserted by means of conventional endoscopic procedures and which has been cut to a desired length by a surgeon. The adaptor is said to comprise an anti-reflux valve assembly having a stem which can be plugged into the open end of the feeding tube. The valve assembly is said to contain a seal which functions as a one-way valve to prevent reflux of gastric contents but which permits the introduction of feeding solution into the feeding tube. A clamp is placed around the feeding tube and the valve stem and is locked into place to secure the valve assembly to the feeding tube at a location flush with the patient's skin. A silicone cover is placed around the clamp to protect the patient from skin irritation caused by the clamp and also to protect the clamp and valve assembly from contaminants.

Although the aforementioned adaptor favorably addresses some of the problems discussed above, the present inventors have identified certain shortcomings associated therewith. One such shortcoming is that the clamp of said adaptor is quite small and, therefore, is difficult to manipulate. Moreover, to insert the valve stem down into the gastrostomy feeding tube and then to attach the clamp around the gastrostomy tube against the valve stem, one must allow for a sufficient externally-extending length to be left in the gastostomy tube so that one can grasp the gastrostomy tube at a point distal to where the valve stem and the clamp are coupled to the tube. (Otherwise, the gastrostomy tube may be pushed completely into the patient, for example, as the valve stem is pushed down into the tube.) This extra length of externally-disposed tubing, however, precludes the clamp from resting flush against the patient when the internal bolster is flush against the stomach. Consequently, either the adaptor is positioned a short distance from the skin, thereby rendering it higher in profile than it otherwise would be, or the distal end of the tube extends a short distance into the stomach, possibly interfering with stomach function.

Another shortcoming is that the clamp has a tendency to pinch the proximal end of the gastrostomy tube at those points where the male and female sections of the clamp are joined. Such pinching, over time, has a tendency to cause the tube to tear. In addition, once the clamp is closed, it cannot be re-opened; consequently, one cannot remove and reattach the valve stem and the clamp from the proximal end of the gastrostomy feeding tube. Accordingly, once the clamp has been closed, one cannot adjust the length of the gastrostomy feeding tube nor can one clean the valve stem or the proximal end of the feeding tube to remove any accumulated debris therewithin. Moreover, one cannot simply eliminate the clamp from the aforementioned adaptor since, in the absence of the clamp, the valve stem, which has a barb-type fitting, can rather easily be pulled out of the feeding tube (i.e., with about a 5 pound pulling force).

Still another shortcoming with the aforementioned adaptor is that the valve assembly of the subject adaptor relies upon the use of a silicone gasket having a Y-shaped slot through which a cannula is typically inserted to deliver food and/or medications. However, such a silicone gasket, after repeated insertions of the cannula therethrough, has a tendency to tear or to otherwise fail to act reliably as a one-way valve. Consequently, because the adaptor cannot easily be disconnected from the gastrostomy feeding tube once connected thereto, replacement of a worn gasket requires the removal and replacement of the gastrostomy feeding tube as well.

Still yet another shortcoming with the aforementioned adaptor is that it possesses a relatively small lumen through which fluid may pass. In addition, due to its manner of operation, the valve tends to get clogged over time, further restricting fluid flow.

Consequently, there is a need for a low profile device that overcomes at least some of the problems discussed above in connection with existing low profile PEG devices, whether of the above-described PEG replacement variety or the above-described PEG convertible variety.

In addition, another drawback that the present inventors have noted with regard to existing PEG devices is that such devices require percutaneous endoscopy for implantation of the initially-placed gastrostomy feeding tube. Although percutaneous endoscopy has many advantages over surgery, it is, nevertheless, a sophisticated technique that requires the use of special equipment, such as an endoscope and a snare. Moreover, the technique can cause infections as the endoscope must be drawn through the mouth and esophagus (where bacteria are prevalent) and into a freshly created wound site. In addition, the technique requires that the endoscope be introduced through the esophagus twice, and the second placement is often very difficult because of damage caused during the first placement. Accordingly, there is additionally a need for a gastrostomy device that does not require the use of percutaneous endoscopy for its implantation in a patient.

Medical catheters other than gastrostomy feeding tubes are known. Examples of such medical catheters include drainage catheters. Many drainage catheter assemblies are designed to include a catheter having a deployable internal bolstering mechanism at its distal end and a locking suture for maintaining the internal bolstering mechanism in its deployed (i.e., opened or anchoring) state. An example of such a drainage catheter assembly is disclosed in U.S. Pat.

No. 5,928,208, inventors Chu et al., which issued Jul. 27, 1999, and which is incorporated herein by reference. Drainage catheters are typically implanted in a patient using either a trocar (or "direct stick") technique or an "over-the-wire" (or Seldinger) technique.

Drainage catheters, particularly those used in conjunction with a locking suture, are not well-suited to be cut to a customized length for low profile use on a patient since the cutting of the catheter could lead to the inadvertent cutting of the suture as well.

SUMMARY OF THE INVENTION

It is an object of the present invention to provide a novel medical catheter assembly.

It is another object of the present invention to provide a medical catheter assembly as described above that overcomes at least some of the problems described above in connection with existing medical catheter assemblies, particularly low profile PEG devices and drainage catheters of the types described above.

Therefore, according to one aspect of the invention, there is provided a medical catheter assembly comprising (a) a medical catheter, said medical catheter having a proximal end, a distal end and a longitudinal bore, said distal end being shaped to include an internal bolster, said internal bolster having an anchoring state and a non-anchoring state; (b) a suture extending from said internal bolster through said longitudinal bore to exit said medical catheter at said proximal end wherein proximal displacement of said suture maintains said internal bolster in said anchoring state; and (c) a protective sleeve made of a rigid material, said protective sleeve being removably insertable into said medical catheter through said proximal end, said suture being inserted through said protective sleeve.

In a preferred embodiment, the aforementioned medical catheter is a gastrostomy feeding tube, the gastrostomy feeding tube having an external circumferential flange at its proximal end and having a malecot structure as its internal bolster. The assembly further includes a body, a clamp, a cap, a trocar assembly and a cannula assembly. The body includes a base portion and a sleeve portion, the base portion being dimensioned to engage the skin of a patient and having a transverse bore, the sleeve portion extending upwardly from the base portion and having a longitudinal slot aligned with the transverse bore and a transverse slot intersecting the longitudinal bore. The top end of the sleeve is shaped to define a barb and is placed in contact with the external circumferential flange of the gastrostomy feeding tube. The clamp, which is slidably mounted on the base portion and across the transverse slot of the sleeve, comprises a plate having a transverse opening. The transverse opening has a wide region alignable with the longitudinal bore and correspondingly dimensioned and a narrow region also alignable with the longitudinal bore. The cannula assembly includes a cannula and a cannula hub, the cannula being removably inserted into the longitudinal bore of the gastrostomy feeding tube and serving to maintain the gastrostomy feeding tube in its non-anchoring state, the cannula hub being fixed to the proximal end of the cannula and being removably secured to the sleeve. The trocar assembly includes a trocar and a trocar hub, the trocar being removably inserted through the cannula and the gastrostomy feeding tube so as to extend distally from the distal end of the gastrostomy feeding tube, the trocar hub being fixed to the proximal end of the trocar and being removably mounted on the cannula hub.

To implant the gastrostomy feeding tube in a patient, the distal ends of the trocar and the gastrostomy feeding tube are directly inserted through the skin and into the stomach of a patient while the internal bolster is held in its non-anchoring state by the cannula. The trocar and cannula assemblies are then removed from the gastrostomy feeding tube, thereby allowing the internal bolster to assume its anchoring state. The base of the body is then brought down into contact with the top of the patient's skin while the gastrostomy feeding tube is pulled upwardly until the internal bolster engages the bottom surface of the patient's stomach wall. The protective sleeve is then slid distally relative to the suture until it is positioned within the gastrostomy feeding tube at that length where the gastrostomy feeding tube is to be cut. The tube is then cut to the desired length, the protective sleeve protecting the suture from inadvertently also being cut. The sleeve is then removed from the tube, and the new proximal end of the tube is then inverted over the top end of the sleeve. With the suture held taut, the cap is then screwed over the thus folded-over proximal end of the tube and onto the sleeve, thereby securing the tube against the barb and the top edge of the sleeve. The cap is provided with an opening through which access to the tube may be gained. With the cap thus secured to the sleeve, the suture is securely retained therebetween, and the protective sleeve may then be removed from the suture by cutting the suture at an appropriate location. By aligning the wide region or the narrow region of the clamp with the longitudinal bore of the sleeve, one can open or close, respectively, the tube to the passage of materials therethrough.

By removing the aforementioned trocar and trocar hub from the subject assembly, the resultant assembly is rendered well-suited for implantation of the gastrostomy feeding tube by an "over-the-wire" technique.

According to another aspect of the invention, there is provided a medical catheter assembly comprising (a) a medical catheter, said medical catheter having a proximal end, a distal end and a longitudinal bore, said distal end being shaped to include an internal bolster, said internal bolster having an anchoring state and a non-anchoring state; (b) a cannula removably inserted into said longitudinal bore of said medical catheter for maintaining said internal bolster in said non-anchoring state; and (c) a body, said body comprising a sleeve, said sleeve having a longitudinal bore through which said medical catheter extends and a top end over which said proximal end of said medical catheter may be inverted.

According to still another aspect of the invention, there is provided a method of percutaneously implanting a gastrostomy feeding tube, said method comprising the steps of (a) providing a gastrostomy feeding tube assembly, said gastrostomy feeding tube assembly comprising (i) a gastrostomy feeding tube, said gastrostomy feeding tube having a proximal end, a distal end and a longitudinal bore, said distal end being shaped to include an internal bolster, said internal bolster having an anchoring state and a non-anchoring state; (ii) a trocar, said trocar having a proximal end and a distal end, said trocar being removably mounted in said gastrostomy feeding tube in such a way as to extend through the distal end of said gastrostomy feeding tube; (b) while said internal bolster is in said non-anchoring state, directly inserting the distal end of said trocar and said internal bolster of said gastrostomy feeding tube through the skin and into the stomach of a patient, said proximal end of said gastrostomy feeding tube not being inserted through the skin of the patient; and (c) then, transforming said internal bolster from said non-anchoring state to said anchoring state.

According to still yet another aspect of the invention, the present invention is directed to a method of percutaneously implanting a gastrostomy feeding tube, said method comprising the steps of (a) providing an entry needle assembly, said entry needle assembly comprising a trocar portion and a cannula portion, said trocar portion being removably inserted through said cannula portion, said trocar portion having a proximal end and a distal end, said cannula portion having a proximal end and a distal end; (b) inserting the distal ends of said trocar portion and said cannula portion of said entry needle assembly through the skin and into the stomach of a patient so as to create a tract; (c) then, removing said trocar portion of said entry needle assembly from the patient while keeping said cannula portion of said entry needle assembly in place; (d) then, inserting a guide wire through said cannula portion of said entry needle assembly and into the patient's stomach; (e) then, removing said cannula portion of said entry needle assembly while keeping said guide wire in place; (f) providing a gastrostomy feeding tube, said gastrostomy feeding tube having a proximal end, a distal end and a longitudinal bore, said distal end being shaped to include an internal bolster, said internal bolster having an anchoring state and a non-anchoring state; (g) then, while said internal bolster is in said non-anchoring state, inserting the gastrostomy feeding tube over the guide wire until said internal bolster is inserted into the stomach of the patient, said proximal end of said gastrostomy feeding tube not being inserted into the patient; and (h) then, transforming said internal bolster from said non-anchoring state to said anchoring state.

According to a further aspect of the invention, there is provided a method of implanting a medical catheter, said method comprising the steps of (a) providing a medical catheter assembly, said medical catheter assembly comprising (i) a medical catheter, said medical catheter having a proximal end, a distal end and a longitudinal bore, said distal end being shaped to include an internal bolster, said internal bolster having an anchoring state and anon-anchoring state; (ii) a suture extending from said internal bolster through said longitudinal bore to exit said medical catheter at said proximal end wherein proximal displacement of said suture maintains said internal bolster in said anchoring state; and (iii) a protective sleeve made of a rigid material, said protective sleeve being removably insertable into said medical catheter through said proximal end, said suture being inserted through said protective sleeve; (b) with the internal bolster in said non-anchoring state, inserting the distal end of said medical catheter into the patient, the proximal end of said medical catheter extending out of the patient; (c) transforming said internal bolster from said non-anchoring state to said anchoring state; (d) inserting the protective sleeve into said medical catheter through said proximal end to a desired depth; (e) then, while maintaining said protective sleeve at said desired depth, cutting the medical catheter at said desired depth to yield a proximal portion and a distal portion of the cut medical catheter; (f) then, removing said protective sleeve from the distal portion of the cut medical catheter; and (g) then, securing the proximal end of the distal portion of the cut medical catheter to an external bolster.

For purposes of the present specification and claims, relational terms like "top," "bottom," "upper," and "lower" are used to describe the present invention in a context in which the catheter is extending upwardly out of a patient. It is to be understood that, by orienting a patient such that the catheter extends outwardly in a direction other than upwardly, the directionality of the invention will need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 2(a) and 2(b) are top and section views of the body shown in FIG. 1, the transverse slot of the body being shown in dotted lines in FIG. 2(a);

FIG. 3 is a bottom view of the clamp shown in FIG. 1;

FIG. 4 is a top view of the cap shown in FIG. 1;

FIGS. 10 and 11 are section views showing how the insertion of the bottom end of a tool down into the proximal end of the gastrostomy feeding tube of FIG. 9 causes said proximal end to flare outwardly;

FIGS. 12(a) and 12(b) are front and enlarged top views, respectively, of the tool of FIGS. 10 and 11;

FIG. 16(b) is a fragmentary front view of the distal end of the low profile medical catheter assembly of FIG. 16(a);

FIG. 17 is a fragmentary front view of the distal end of the low profile medical catheter assembly of FIG. 16(a), with the tube in its axially-compressed, radially-expanded, anchoring state;

FIG. 18(b) is a fragmentary front view of the distal end of the low profile medical catheter assembly of FIG. 18(a);

DETAILED DESCRIPTION OF PREFERRED EMBODIMENTS

Figures 1, 1A:
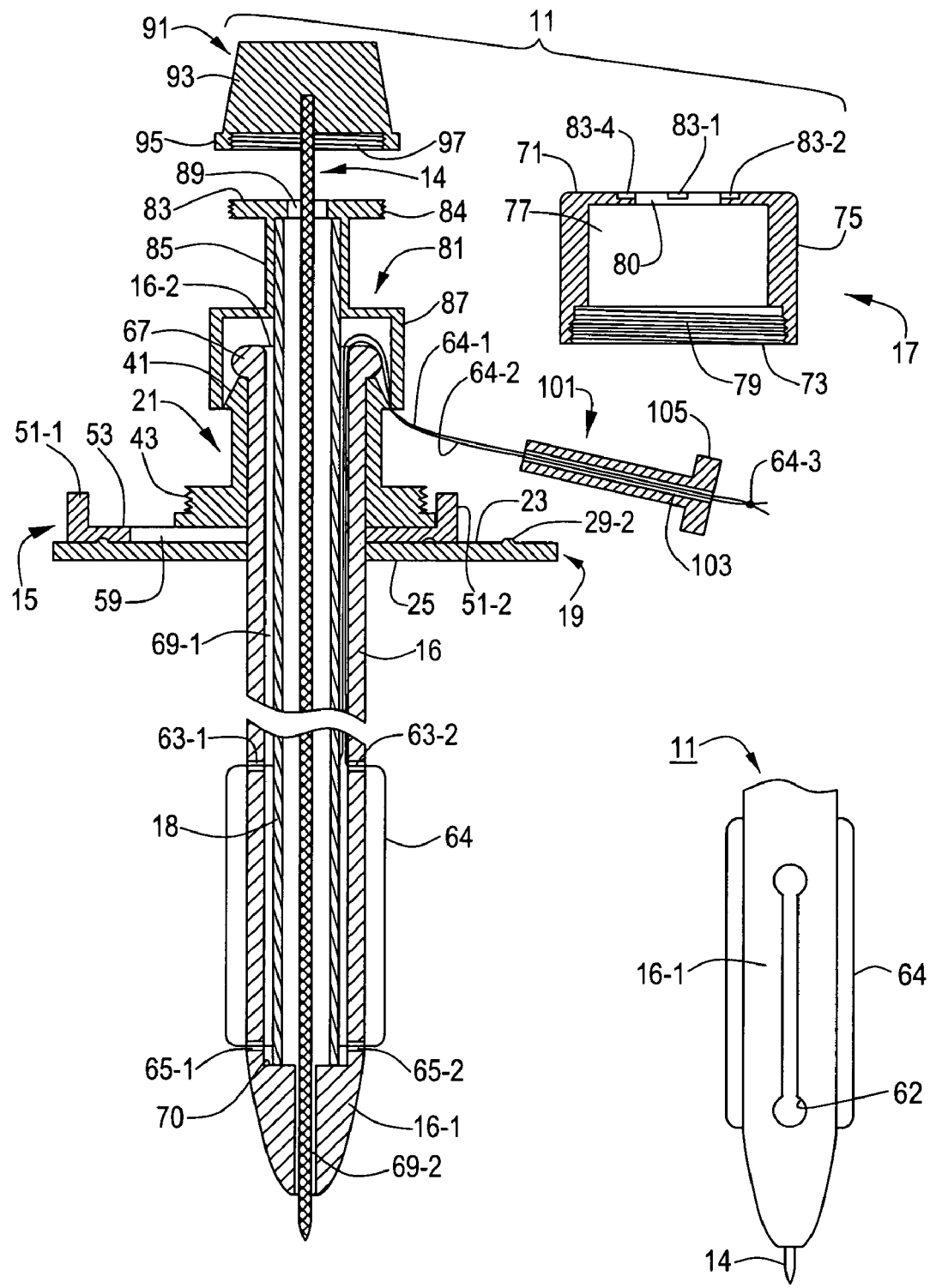
FIG. 1 is a partially exploded, fragmentary, section view of a first embodiment of a low profile medical catheter assembly constructed according to the teachings of the present invention.
FIG. 1(a) is a fragmentary front view of the distal end of the low profile medical catheter assembly of FIG. 1.

Referring now to FIG. 1, there is shown a partially exploded, fragmentary, section view of a first embodiment of a low profile medical catheter assembly constructed according to the teachings of the present invention, said low profile medical catheter assembly being represented generally by reference numeral 11.

Assembly 11, which is shown prior to use on a patient, comprises a body 13, a trocar 14, a clamp 15, a gastrostomy feeding tube 16, a cap 17, and a cannula 18.

Referring now to FIGS. 2(a) and 2(b), body 13, which is a unitary structure preferably made of molded medical grade plastic, is shaped to include a base 19 and a sleeve 21. Base 19, which is appropriately sized to engage the skin of the patient so as to serve as an external bolster, is a quasi-rectangular member having a pair of straight sides 20-1 and 20-2, a pair of rounded ends 22-1 and 22-2, a top surface 23, a bottom surface 25 and a centrally-disposed transverse bore 27. A pair of detents 29-1 and 29-2 are formed on top surface 23 along its longitudinal centerline, the purpose of detents 29-1 and 29-2 to be discussed below.

Sleeve 21 is an elongated tubular member that extends upwardly from top surface 23, sleeve 21 having an open top end 31, an open bottom end, a generally circular side wall 35, a longitudinal bore 37 and a transverse slot 39. For reasons to be discussed below, the top portion of side wall 35 is shaped to define an upwardly-directed external barb 41. For reasons also to be discussed below, an intermediate portion of side wall 35 is shaped to include an external helical thread 43. Longitudinal bore 37 is aligned with transverse bore 27 of base 19 and is substantially equal in diameter thereto. Transverse slot 39, which is formed in the bottom portion of side wall 35 and runs generally parallel to the length of base 19, intersects longitudinal bore 37 for reasons to be discussed below.

Referring now to FIGS. 1 and 3, clamp 15, which is preferably made of molded medical grade plastic, is an elongated, quasi-rectangular slide having a pair of straight sides 50-1 and 50-2, a pair of rounded, turned-up ends 51-1 and 51-2, a top surface 53, a bottom surface 55, and a transverse opening 56. Transverse opening 56 comprises a wide circular region 57 and a narrow slit region 59. For reasons to become apparent below, wide circular region 57 is substantially equal in size to bores 27 and 37 whereas narrow slit region 59 is much smaller in size than bores 27 and 37. A pair of recesses 61-1 and 61-2 are provided in bottom surface 55 of clamp 15, recess 61-1 being adapted to receive detent 29-1 to maintain clamp 15, when desired, in an open position, recess 61-2 being adapted to receive detent 29-2 to maintain clamp 15, when desired, in a closed position.

Clamp 15 is slidably mounted on base 19 and across slot 39 and is movable between (i) an open position in which circular region 57 is aligned with bores 27 and 37, and detent 29-1 is received in recess 61-1 and (ii) a closed position in which slit region 59 is aligned with bores 27 and 37, and detent 29-2 is received in recess 61-2.

Referring now to FIGS. 1 and 1(a), gastrostomy feeding tube 16 comprises an open distal end 16-1, an open proximal end 16-2 and a longitudinal bore. Distal end 16-1, which is shaped to have a malecot structure defining a transverse slit 62 and which terminates in a relatively sharp tip, is provided with opposing pairs of side openings 63-1/63-2 and 65-1/65-2 through which a locking suture 64 is looped in a conventional manner, with ends 64-1 and 64-2 of suture 64 extending through proximal end 16-2 of tube 16. (The malecot structure of distal end 16-1 may be formed by molding or by thermo-shaping a cut tube.) Proximal end 16-2 is shaped to include an external circumferential flange or bump 67, the purpose of which will be described below. The longitudinal bore of tube 16 comprises a proximate portion 69-1 and a distal portion 69-2, proximate portion 69-1 extending nearly the entire length of tube 16 and having a comparatively greater diameter that is adapted for receiving cannula 18, distal portion 69-2 extending distally from the distal end 70 of proximate portion 69-1 and having a comparatively lesser diameter that is adapted for receiving trocar 14.

Tube 16 is appropriately dimensioned for insertion through bore 27 of base 19, opening 56 of clamp 15 and bore 37 of sleeve 21 while, at the same time, being sufficiently small in outer diameter and stiff to permit its direct insertion through a patient's skin. When clamp 15 is in its open position, tube 16 is disposed within opening 57, opening 57 allowing tube 16 to open to its full inner diameter. When, however, clamp 15 is in its closed position, tube 16 is disposed within slit 59, slit 59 compressing tube 16 to closure.

Referring now to FIGS. 1 and 4, cap 17, which is a unitary member preferably made of molded medical grade plastic, comprises a top wall 71, an open bottom 73, a circular side wall 75 and a cylindrical cavity 77, cylindrical cavity 77 being circumferentially bounded by side wall 75. The bottom portion of side wall 75 has a decreased cross-sectional thickness, and a helical thread 79 is formed on the inside surface thereof so that, as will be described below, cap 17 may be removably mounted over the proximal end of tube 16 and onto body 13, with thread 79 matingly engaging thread 43 of sleeve 21. A transverse opening 80 having a diameter substantially equal to proximal portion 69-1 of the longitudinal bore of tube 16 is provided in top wall 71, opening 80 being aligned with proximal portion 69-1 when cap 17 is mounted thereover. A plurality of recesses 83-1 through 83-4 equidistantly spaced around the perimeter of opening 80 are provided in the top surface of top wall 71, the purpose of recesses 83-1 through 83-4 to be discussed below.

As will be seen below, cap 17 serves to secure the proximal end of tube 16 against barb 41 and against the top edge 40 of sleeve 21, thereby increasing the grip strength of the device to at least 18 pounds. It is also to be noted that the compression of tube 16 by cap 17 against sleeve 21 creates a tight seal between tube 16 and a fitting inserted thereinto.

Referring now to FIG. 1, assembly 11 further comprises a cannula hub 81, cannula hub 81 being a unitary member comprising an upper portion 83, an intermediate portion 85 and a lower portion 87. Upper portion 83, which is annular in shape, includes a central opening 89 through which trocar 14 is permitted to pass. A helical thread 84, whose purpose will be described below, is formed on the outer side surface of upper portion 83. Intermediate portion 85, which is tubular in shape, includes a longitudinal bore that has an inside diameter greater than the diameter of opening 89, said longitudinal bore being coaxial with opening 89. Intermediate portion 85 is adapted to securely receive the proximal portion of cannula 18, with the proximal end of cannula 18 abutting the bottom surface of upper portion 83. Lower portion 87, which is tubular in shape and coaxial with intermediate portion 85, has an inside diameter greater than that of intermediate portion 85. Lower portion 87 is appropriately sized to receive the proximal end 16-2 of tube 16 and to securely fit around barb 41 of sleeve 21 while, at the same time, permitting suture 64 to pass through the open bottom end thereof.

Assembly 11 additionally comprises a trocar hub 91, trocar hub 91 being a unitary member shaped to include a body 93 and a collar 95. Body 93 is fixedly secured to the proximal end of trocar 14 and facilitates the manipulation of trocar 14. A helical thread 97 is formed on the inside surface of collar 95, thread 97 being threadingly engageable with thread 84 on the upper portion 83 of cannula hub 81 to permit trocar hub 91 to be removably coupled to cannula hub 81.

Assembly 11 further comprises a protective sleeve 101, the purpose of which will be described below. Sleeve 101, which is a unitary member preferably made of a metal or a hard medical grade plastic, is shaped to include a longitudinal bore 103, bore 103 being appropriately sized to enable much of the length of suture 64 to pass therethrough while preventing knot 64-3 of suture 64 from passing therethrough. Sleeve 101 is also shaped to include a flange 105 at its proximal end, flange 105 being adapted to rest on top of proximal end 16-2 of tube 16 for reasons to become apparent below.

Figure 5A:
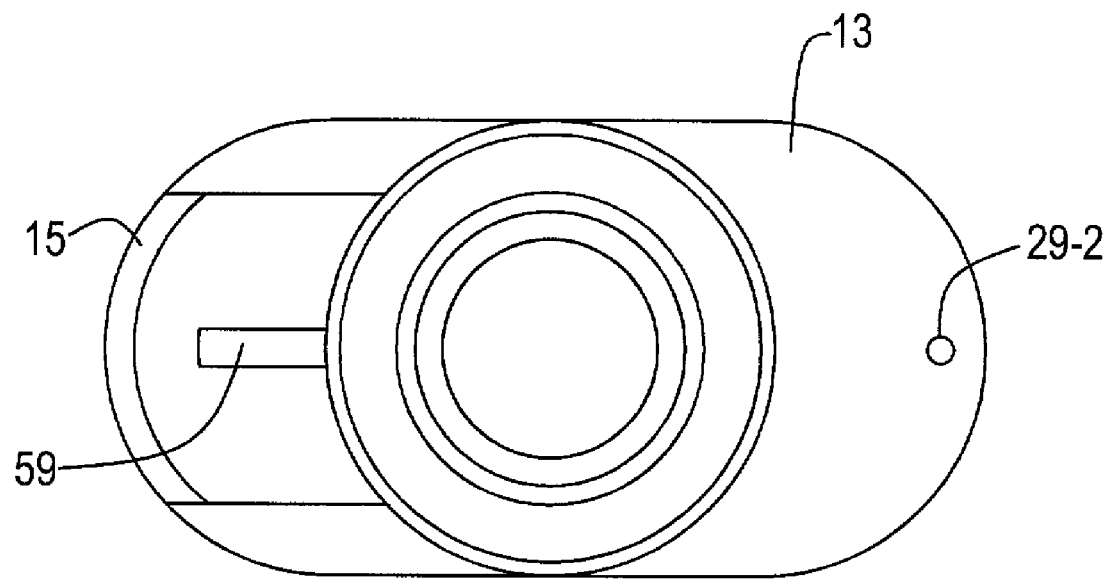
FIGS. 5(a) and 5(b) are top and section views, respectively, of the body and the clamp of FIG. 1 shown in an assembled state, with the clamp in an open position.
Figure 5B:
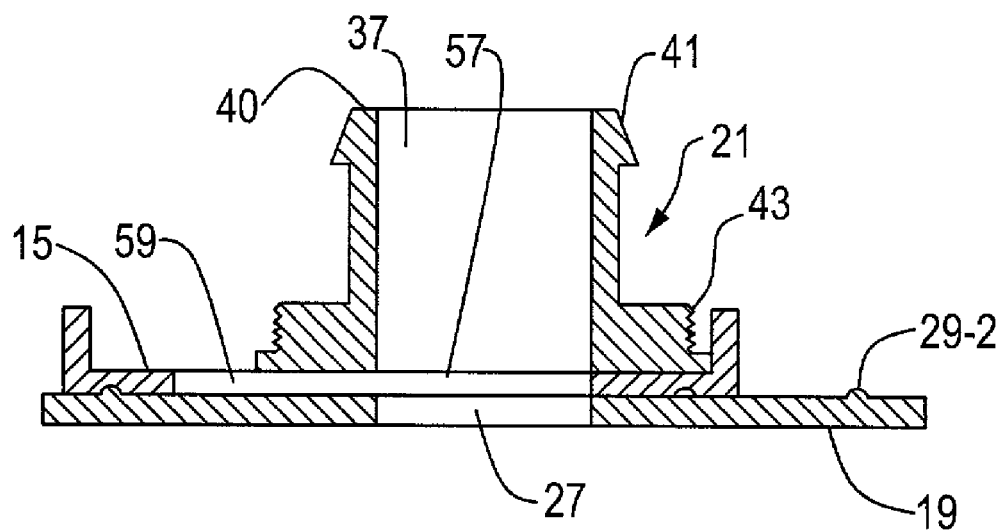

To prepare assembly 11 for use, clamp 15 is positioned within slot 39 of body 13 in its open position so that circular region 57 is aligned with bores 27 and 37 and so that detent 29-1 is received in recess 61-1 (see FIGS. 5(a) and 5(b)). Next, distal end 16-1 of tube 16 is inserted down through bore 27, circular region 57, and bore 37, respectively, until bump 67 of tube 16 is brought into contact with top edge 40 of sleeve 21. Cannula 18, which is made of a rigid or semi-rigid metal or plastic, is then inserted down into proximal portion 69-1 of tube 16 until the distal end of cannula 18 contacts distal end 70 of proximal portion 69-1 and causes the malecot structure of tube 16 to be straightened into a tubular form (i.e., a non-anchoring state). Ends 64-1 and 64-2 of suture 64 are drawn out of tube 16 past bump 67 and sleeve 21, and lower portion 87 of cannula hub 81 is then secured to sleeve 21. Ends 64-1 and 64-2 of suture 64 are then threaded through tube 101, and knot 64-3 is formed. Trocar 14, the proximal end of which is fixed to trocar hub 91, is then inserted down through opening 89 of hub 81, cannula 18 and distal portion 69-2 of the bore of tube 16, respectively, until trocar hub 91 is mated to cannula hub 81.

Instead of being assembled in the manner described above, assembly 11 may be partially assembled at the time of manufacture into two assembled subassemblies, said first assembled subassembly comprising body 13, clamp 15, tube 16, suture 64 and tube 101, said second assembled subassembly comprising trocar 14, trocar hub 91, cannula 18, and cannula hub 81. The two assembled subassemblies described above may then be coupled together by a physician or the like to yield fully assembled assembly 11 directly before use.

Figure 6:
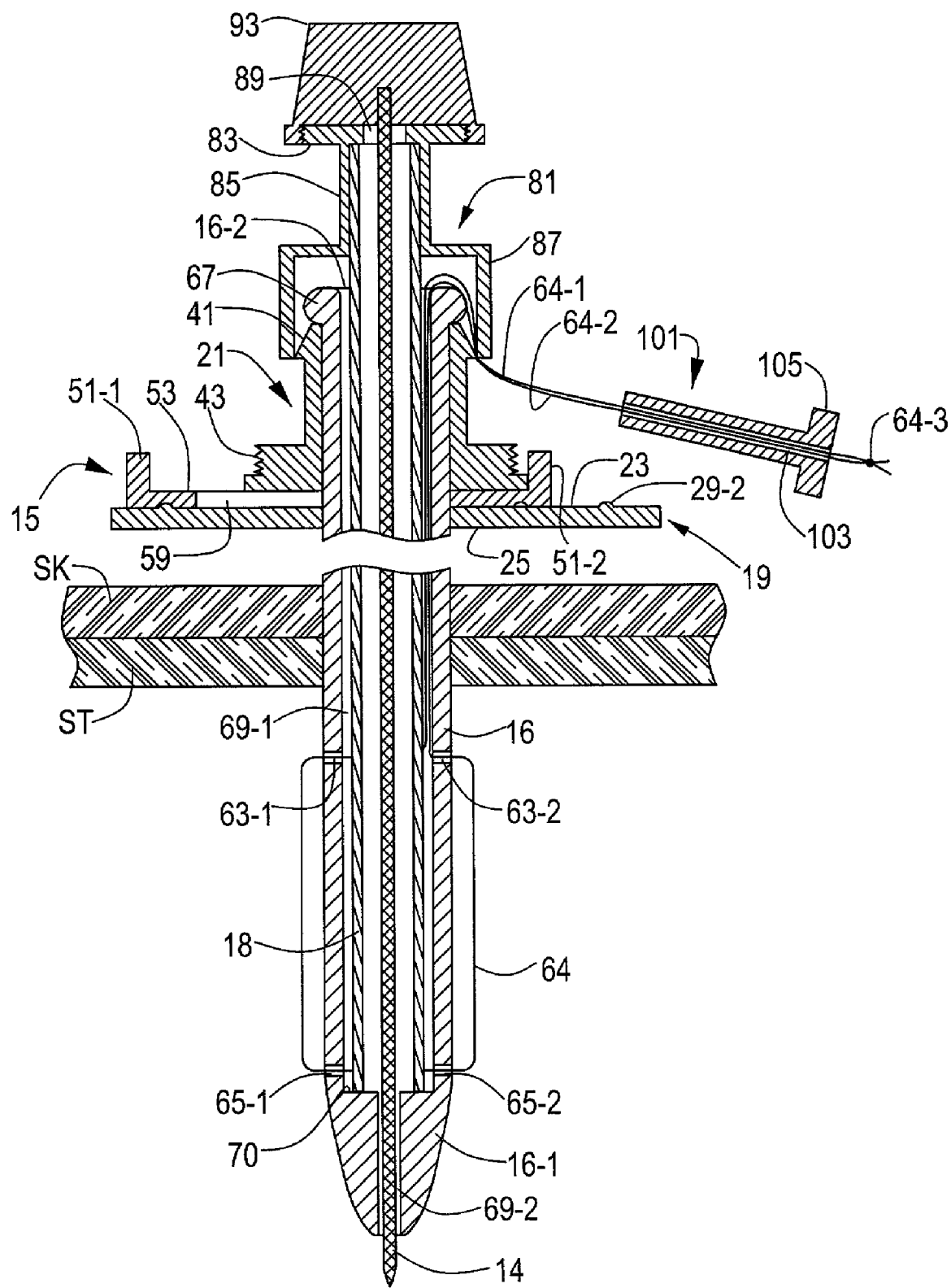
FIG. 6 is a section view showing the assembly of FIG. 1, excluding the cap thereof, being introduced into a patient using a "direct stick" technique.
Figure 7:
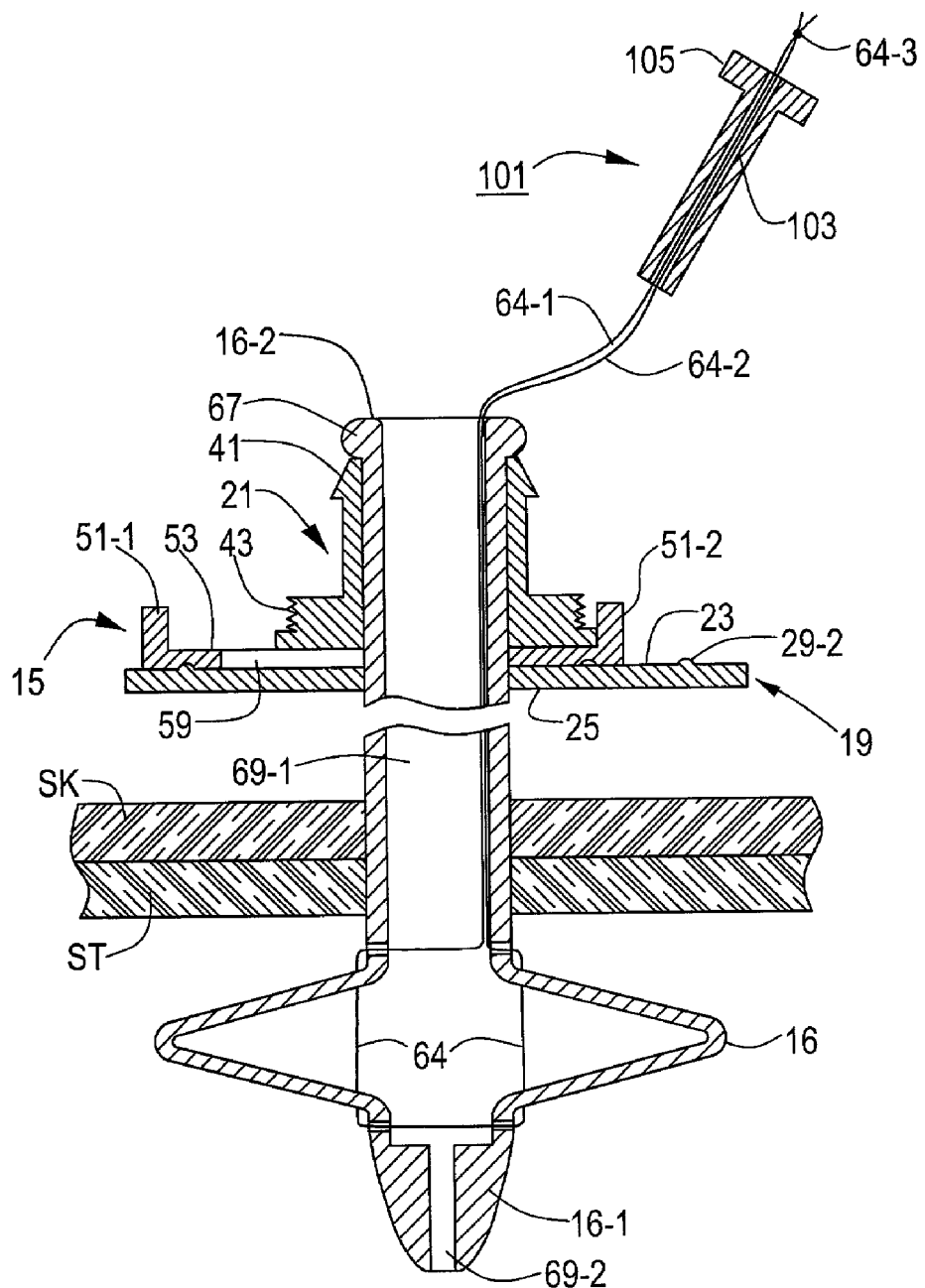
FIG. 7 is a section view showing the assembly of FIG. 6 after the trocar and cannula subassemblies thereof have been removed.

Referring now to FIG. 6, assembly 11, thus prepared for use, is then inserted directly through the skin SK and the stomach wall ST of a patient using the distal end of trocar 14 (i.e., using a "direct stick" technique). To facilitate locating the patient's stomach so that an appropriate insertion site for trocar 14 may be identified, the patient may drink a radiopaque solution to permit the stomach to be seen using a fluoroscope. Alternatively, an endoscope may be inserted into the patient's stomach to shine a light through the stomach wall or to provide an object that can be felt externally. Next, as seen in FIG. 7, trocar 14, trocar hub 91, cannula 18 and cannula hub 81 are then removed from tube 16. The removal of cannula 18 from tube 16 causes the malecot structure of tube 16 to return to its anchoring state, i.e., folded. The excess distal suture 64 is then pulled taut by pulling sleeve 101 up away from proximal end 16-2 of tube 16.

Figure 8:
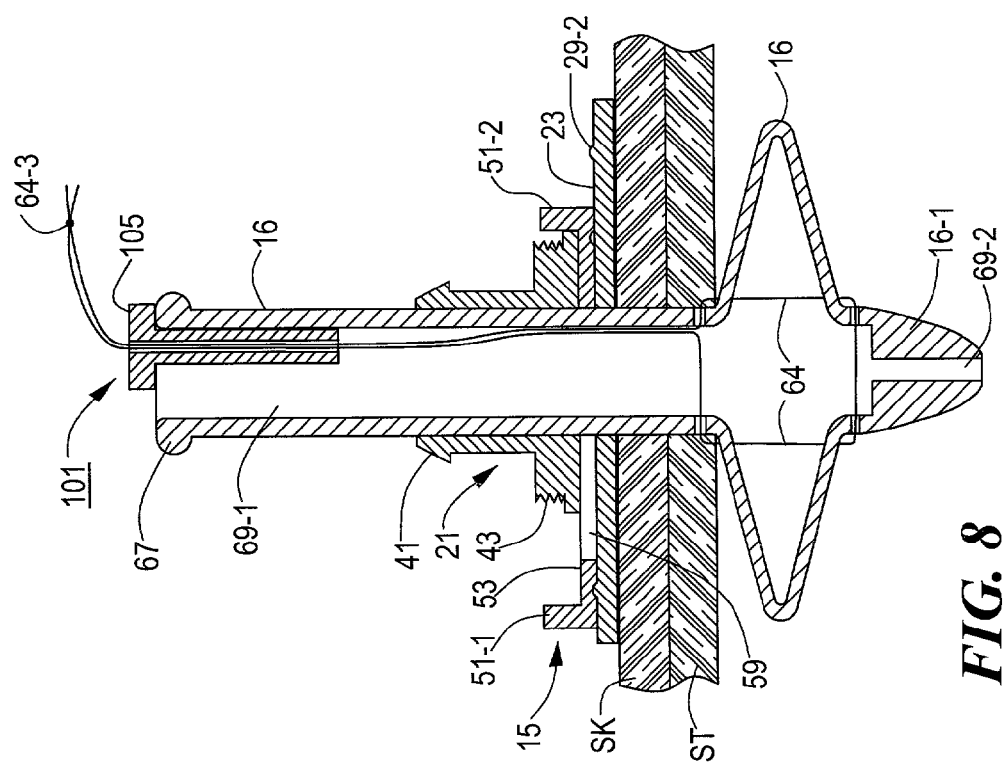
FIG. 8 is a section view showing the assembly of FIG. 7, with the suture protecting sleeve thereof positioned inside of the gastrostomy feeding tube.

Next, as seen in FIG. 8, while keeping suture 64 taut, base 19 is held down against the top of the patient's skin SK and tube 16 is pulled upwardly until the malecot structure of distal end 16-1 engages the patient's stomach wall ST. A marking (not shown) may be made by the physician on the tube to indicate the length to which the tube is to be cut so that its new proximal end will lie in a low profile as further described below. Sleeve 101 is then slid distally relative to suture 64 until it is positioned within tube 16 at said length where tube 16 is to be cut.

Figure 9:
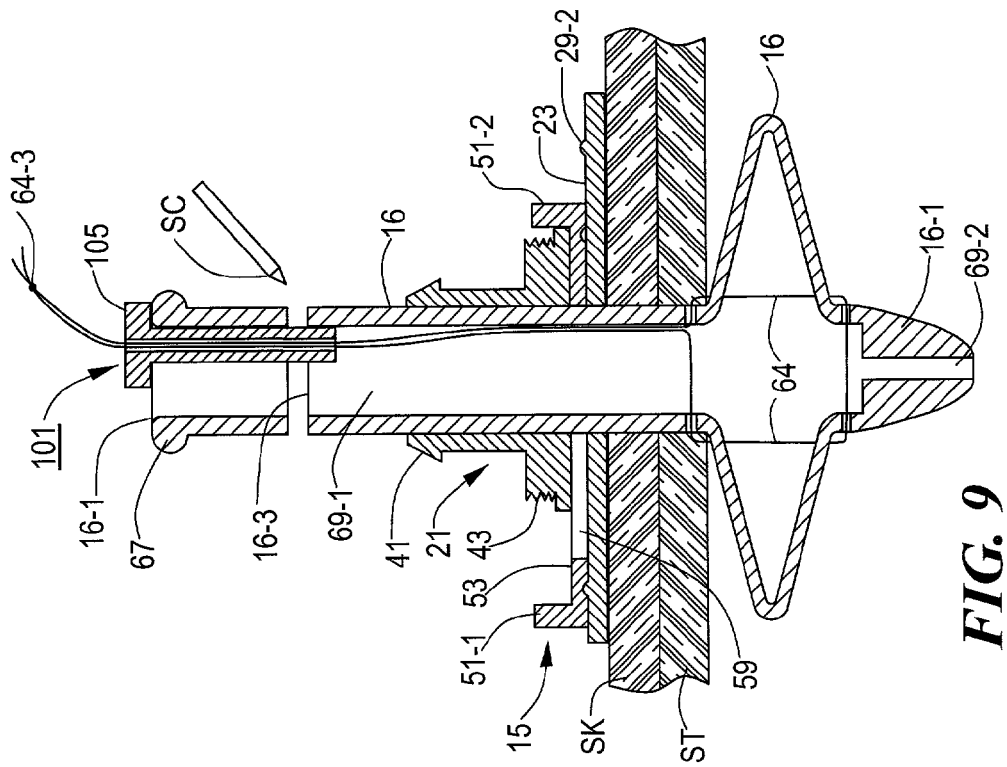
FIG. 9 is a section view illustrating how the suture protecting sleeve protects the suture from being inadvertently cut while the gastrostomy feeding tube is being cut to a desired length.

Next, as seen in FIG. 9, tube 16 is then cut to the desired length using a scalpel SC or the like. (When cutting tube 16 to the desired length, it is desirable to provide some tube length for stomach expansion and/or for cleaning under base 19.) Because sleeve 101 is positioned within tube 16 at the point at which the cut is made, suture 64 is protected against inadvertently being cut. (It should be noted that, whereas in the present embodiment flange 105 serves to prevent sleeve 101 from being inserted too far down into tube 16, this same objective could alternatively be achieved by sizing sleeve 101 to have an outer diameter approximating the inner diameter of tube 16.)

Figure 10:
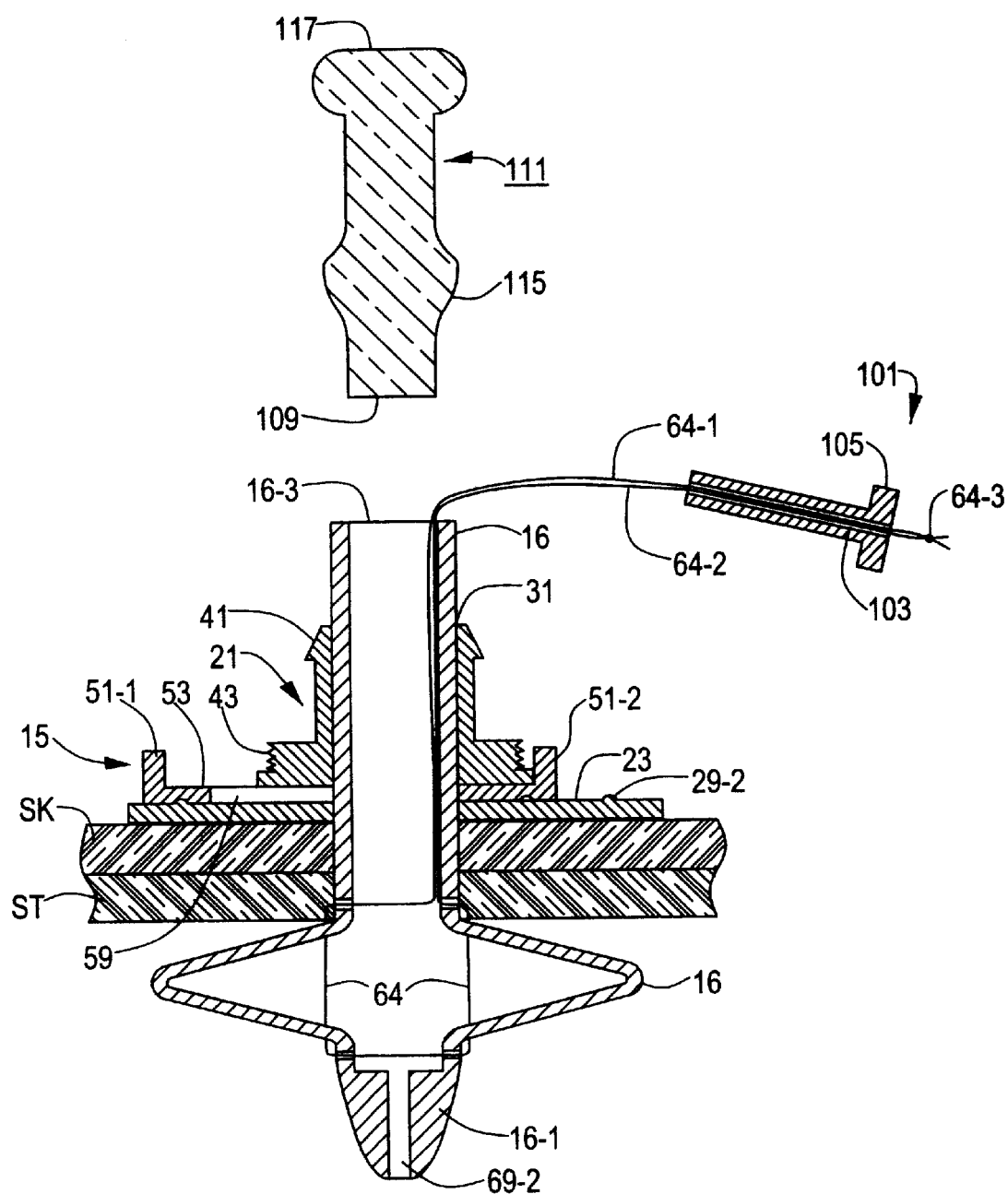

Next, as seen in FIG. 10 and 11, sleeve 101 is removed from tube 16, and the bottom end 109 of a tool 111 (tool 111 being shown separately in FIGS. 12(a) and 12(b)) is then inserted down into the new proximal end 16-3 of tube 16 and into open top end 31 of sleeve 21. Tool 111 has an intermediate portion 115 that flares outwardly from bottom end 109 to a diameter that is greater than the inner diameter of sleeve 21 and that approaches the outer diameter of barb 41. Consequently, the insertion of bottom end 109 of tool 111 into new proximal end 16-3 of tube 16 causes new proximal end 16-3 of tube 16 to flare outwardly.

Figure 13:
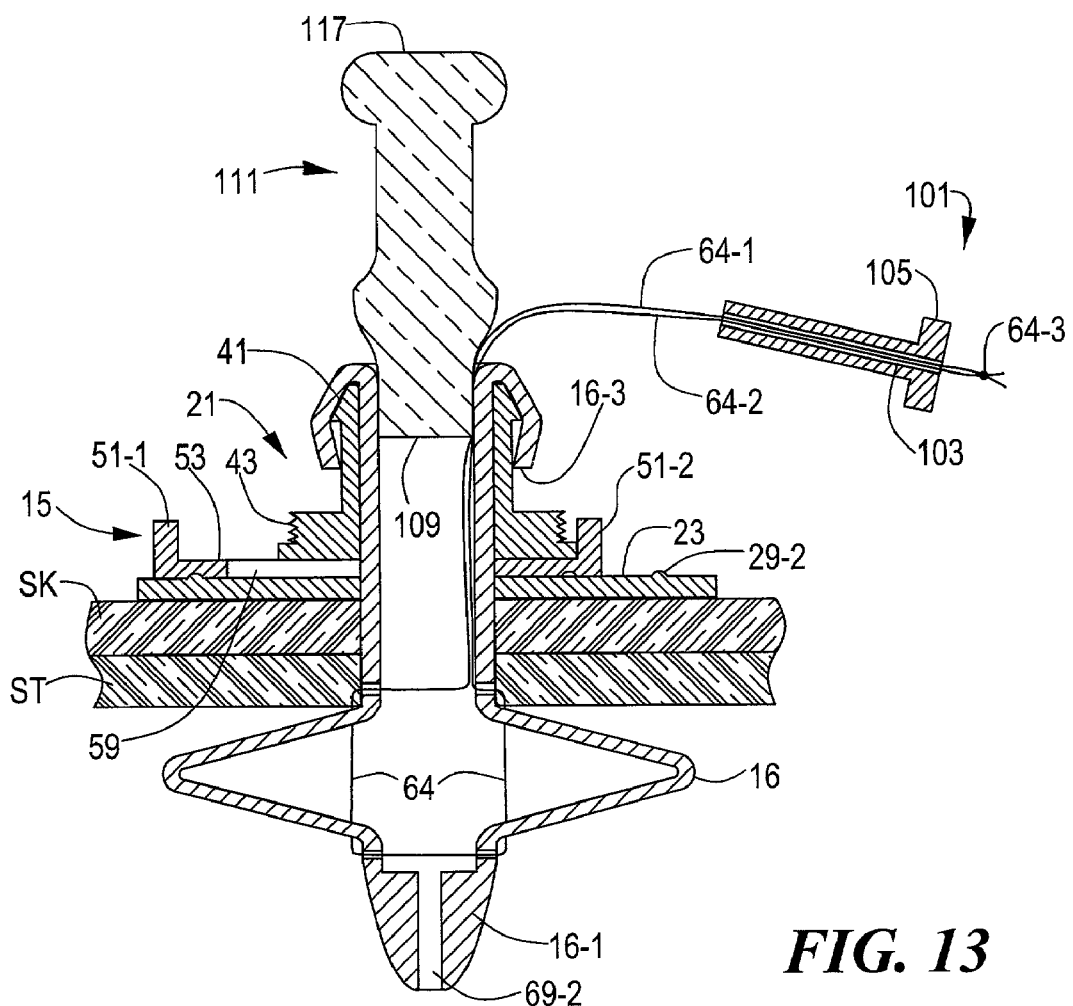
FIG. 13 is a section view showing the proximal end of the gastrostomy feeding tube of FIG. 11 folded over the barbed portion of the body.

Next, as seen in FIG. 13, new proximal end 16-3 of tube 16 is then folded over barb 41 of sleeve 21. This may be done simply by rolling new proximal end 16-3 of tube 16 down off intermediate portion 115 of tool 111 using the thumb and forefinger of one hand. As can be appreciated, the engagement of the new proximal end 16-3 of the tube 16 by barb 41 inhibits, to a certain degree, withdrawal of the tube 16 from sleeve 21.

Figure 14:
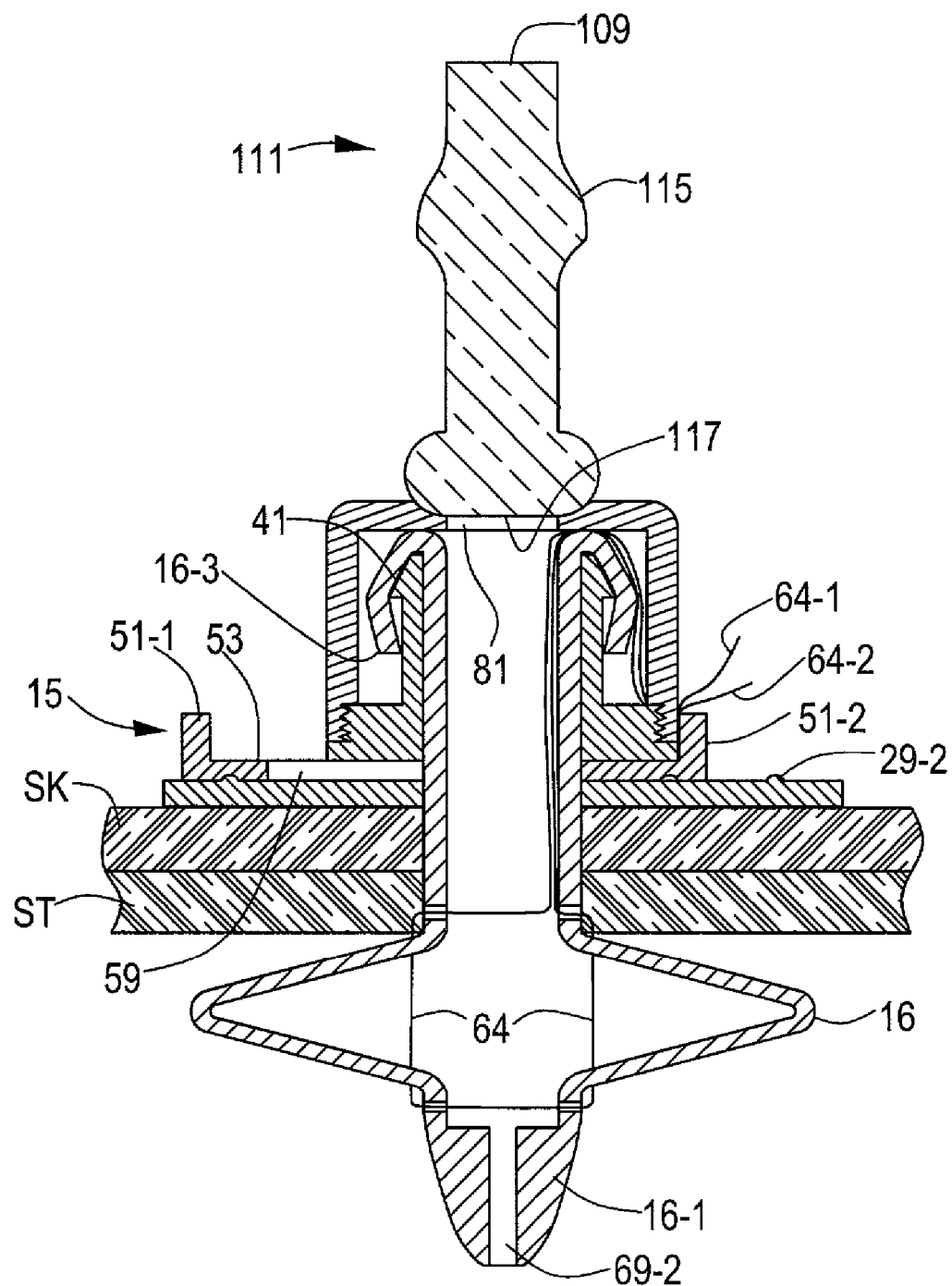
FIG. 14 is a section view showing the top end of the tool of FIGS. 12(a) and 12(b) being used to screw the cap of FIG. 1 over the combination of the proximal end of the gastrostomy feeding tube and the body shown in FIG. 13.

Next, as seen in FIG. 14, while suture 64 is held taut, cap 17 is positioned over the thus folded-over new proximal end 16-3 of tube 16. The top end 117 of tool 111, which has a shape similar to a Phillips head screwdriver, is then inserted into recesses 83-1 through 83-4 and is used to screw cap 17 onto sleeve 21, thereby securing tube 16 against barb 41 and against the top edge 40 of sleeve 21 to a grip strength of at least 18 pounds. (It should be noted that, although cap 17 and sleeve 21 are secured to one another in the present embodiment by threads 79 and 43, respectively, cap 17 and sleeve 21 could alternatively be removably secured to one another by other suitable means.) With cap 17 thus secured to sleeve 21, suture 64 is securely retained therebetween, and sleeve 101 may then be removed from suture 64 by cutting suture 64 at an appropriate location.

To then convey food and/or medications to the patient, tool 111 is removed from opening, a delivery tube/connector is inserted down through opening 80 and into tube 16, clamp 15 is moved from its closed position to its open position, and the food and/or medications are then dispensed into tube 16 (exiting tube 16 via slit 62). It is to be noted that the compression of tube 16 by cap 17 against sleeve 21 creates a tight seal between the delivery tube/connector and tube 16. When the dispensing of the food and/or medications is complete, the delivery tube/connector is withdrawn from tube 16 and opening 80, and clamp 15 is moved back from its open position to its closed position, whereby slit 59 causes tube 16 to be compressed or pinched to an extent that fluid cannot flow therethrough. Consequently, said pinching or compression of tube 16 by slit 59 effectively acts as a valve to prevent the escape of gastric fluids from the patient. It should be noted that the presence of suture 64 in tube 16 does not affect the ability of clamp 15 to cause the closure of tube 16 nor does the presence of suture 64 in tube 16 restrict the flow of materials through tube 16.

As can be appreciated, assembly 11 possesses a number of significant features, some of which are not possessed by existing medical catheter assemblies. One such feature is that tube 16 is attached to body 13 by inserting the proximal end of tube 16 up through body 13 and then folding the proximal end of tube 16 down over the top of body 13, thereby obviating the need for the operator to hold tube 16 from below body 13 when securing tube 16 to body 13.

Another feature is that tube 16 is secured to body 13 in a 360 degree manner. This minimizes the chance that an uneven distribution of retentive force will be applied to the tube, causing the tube to tear. Another such feature is that tube 16 is capable of being detached from and then re-attached to body 13, thereby permitting the length of tube 16 to be adjusted and/or permitting the body 13 and tube 16 to be cleaned of debris. Still another feature, noted above, is that cap 17 secures tube 16 to body 13 with a considerable retentive force. Specifically, the present invention is able to withstand a pulling force of approximately 18 pounds without compromising the quality of the seal between tube 16 and body 13. Still yet another feature is that cap 17 is designed to be screwed and/or unscrewed with a mating tool. This minimizes the possibility that the patient will inadvertently unscrew cap 17. Still a further feature is that a manual valve (i.e., clamp 15) is employed to open and close tube 16, said manual valve permitting tube 16 to have its full inner diameter when in its open state. This maximizes the amount of food and/or medications that can be delivered and minimizes the possibility that tube 16 will become clogged. Still yet a further feature is that no part of body 13 is inserted below the skin surface, thereby allowing the stoma tract created in the patient to be kept at its minimum size. Still even a further feature is that a delivery tube/connector can be coupled to tube 16 while clamp 15 is in its closed position and that clamp 15 can be switched from its open position to its closed position before removing the delivery tube/connector from tube 16. This feature prevents spills, leakage and/or gastric reflux of stomach contents. Still even yet a further feature is that the delivery tube/connector can be inserted directly into tube 16, with tube 16 forming a seal directly around the delivery tube/connector. This reduces the number of parts required. Even still yet a further feature is that the present invention could be used to securely position a guide wire or catheter in a patient's stomach. This may be done, for example, by inserting said guide wire or catheter through proximal and distal portions 69-1 and 69-2, respectively, of tube 16 and into the patient's stomach and then by positioning clamp 15 in its closed position. Such a guide wire could then be used, for example, for placement of a catheter into the gastrointestinal tract. Such a catheter could be used, for example, to deliver a dye or medication or to perform diagnostic and/or interventional procedures.

Although assembly 11 has been described herein in the context of low profile gastrostomy feeding, it should be understood that assembly 11 is not limited to low profile gastrostomy feeding and could be used for high profile gastrostomy feeding. Moreover, apart from whether assembly 11 is used in a low profile or a high profile, assembly 11 is not limited to gastrostomy feeding and may be used for other types of feeding, as well as for drainage.

As noted above, assembly 11 is designed for insertion of tube 16 into a patient by a "direct stick" technique. However, by removing trocar 14 and trocar hub 91 from assembly 11, assembly 11 is rendered particularly well-suited for insertion of tube 16 into a patient by an "over-the-wire" technique. Such an "over-the-wire" technique would involve, for example, inserting a small gauge entry needle assembly into a patient's stomach (with determination of a suitable insertion site of the entry needle assembly aided, if desired, by endoscopic light or a fluoroscope in the manner described above), removing the needle portion of the entry needle assembly from the patient while keeping the cannula portion of the entry needle assembly in place, inserting a guide wire (e.g., a 0.038 inch diameter guide wire) through said cannula portion of the entry needle assembly and into the patient's stomach, removing said cannula portion of the entry needle assembly while keeping the guide wire in place, sequentially using a series of rigid or semi-rigid dilators of increasing diameter (e.g., a series of 8/12/14 french dilators) to dilate the tract made by the entry needle assembly, and then inserting tube 16 over the guide wire, through the dilated tract, and into the patient.

The insertion hole created by the entry needle assembly of the aforementioned "over-the-wire" technique is smaller in diameter (prior to dilation) than the corresponding hole created by the trocar and tube of the above-described "direct stick" technique. This may be advantageous if more than one insertion is necessary, i.e., if the initial insertion is improperly placed on the patient. Another advantage of the "over-the-wire" technique, as compared to the "direct stick" technique, is that catheter insertion and penetration is ensured. This is because the entry site is dilated to fit the larger sized diameter catheters, and the size of the entry site is increased by controlled increased dilations.

Figure 15:
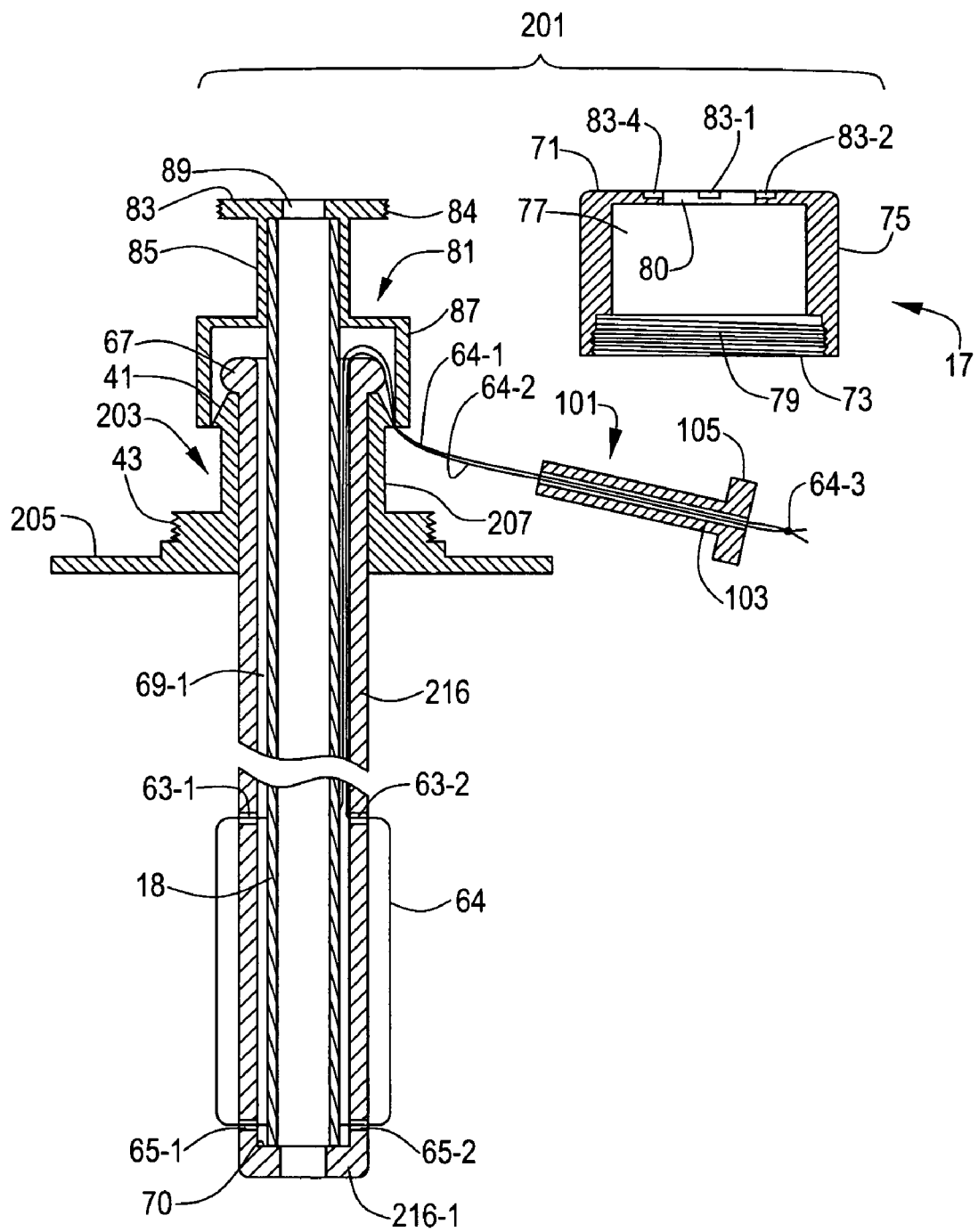
FIG. 15 is a partially exploded, fragmentary, section view of a second embodiment of a low profile medical catheter assembly constructed according to the teachings of the present invention.

Referring now to FIG. 15, there is shown a partially exploded, fragmentary, section view of a second embodiment of a low profile medical catheter assembly constructed according to the teachings of the present invention, said low profile medical catheter assembly being represented generally by reference numeral 201.

Assembly 201 is similar in most respects to assembly 11, the principal differences between the two assemblies being that (i) assembly 201 comprises a body 203, instead of body 13; (ii) assembly 201 does not include clamp 15; (iii) assembly 201 does not include trocar 14 or trocar hub 91; and (iii) assembly comprises a tube 216, instead of tube 16.

Body 203, which is similar in most respects to body 13, includes a base 205 and a sleeve 207. Base 205 is identical to base 19, except that base 205 does not include detents 29-1 and 29-2. Sleeve 207 is identical to sleeve 21, except that sleeve 207 does not include lateral slot 39.

Tube 216, which is similar in many respects to tube 16, differs from tube 16 in that it has a blunt distal end 216-1 with a larger through lumen. Also, because assembly 201 does not include a trocar and, therefore, is not inserted using a "direct stick" technique, but rather, is implanted using the above-described "over-the-wire" technique (in which a plurality of dilators of increasing size are used to dilate the tract into which tube 16 is inserted), tube 216 need not be as axially stiff as tube 16 and need not have as small an outer diameter as tube 16.

Once implanted, assembly 201 may be used in the same manner as described above for assembly 11 (except that, due to the absence of clamp 15, tube 216 cannot be opened and clamped shut in the same way as tube 16).

Figure 16A:
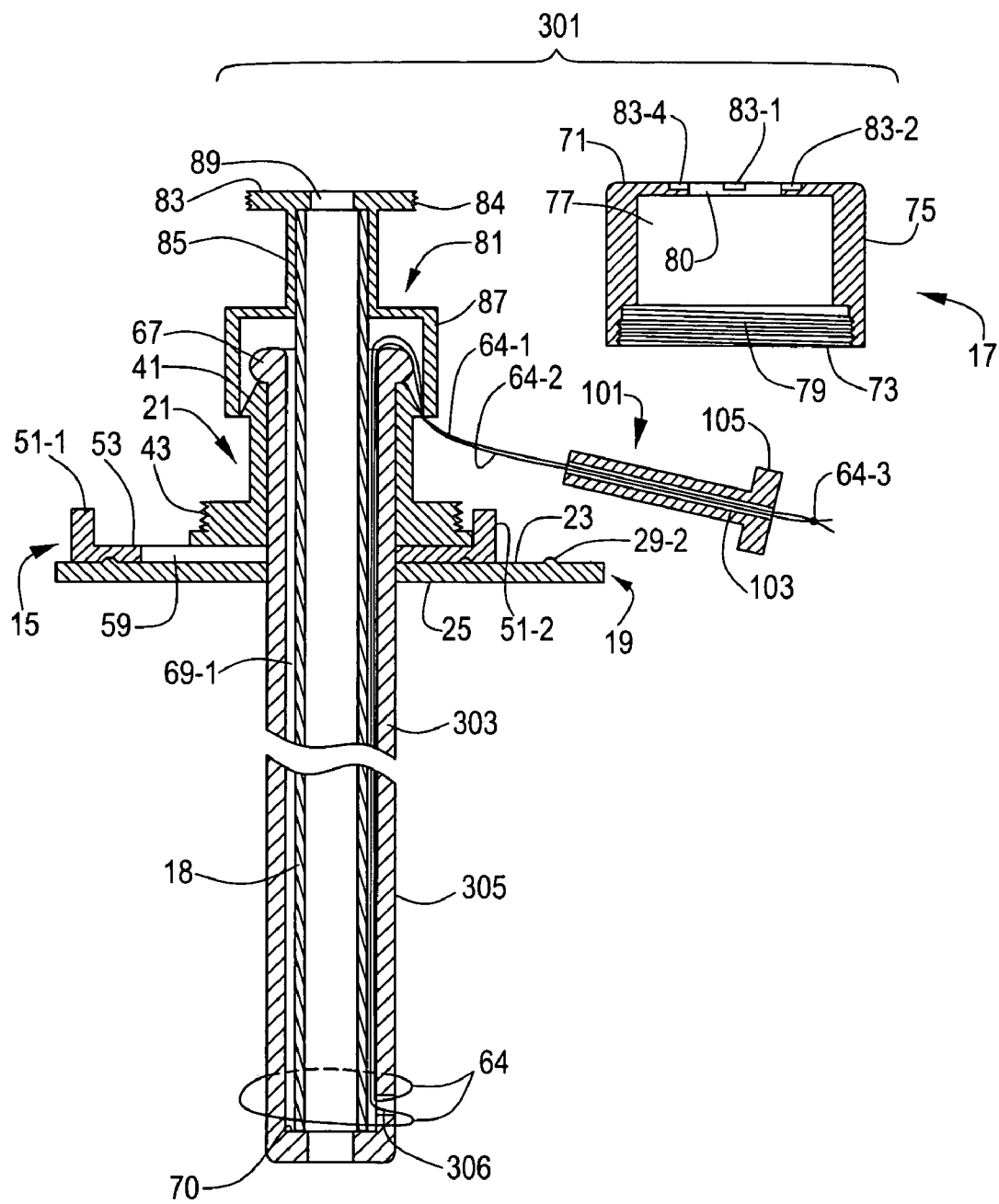
FIG. 16(a) is a partially exploded, fragmentary, section view of a third embodiment of a low profile medical catheter assembly constructed according to the teachings of the present invention.

Referring now to FIGS. 16(*a*) and 16(*b*), there are shown partially exploded, fragmentary, section and fragmentary front views, respectively, of a third embodiment of a low profile medical catheter assembly constructed according to the teachings of the present invention, said low profile medical catheter assembly being represented generally by reference numeral 301.

Assembly 301 is similar in most respects to assembly 11, the principal differences between the two assemblies being that (i) assembly 301 does not include trocar 14 or trocar hub 91; and (ii) assembly 301 includes a blunt-end tube 303 having an axially-collapsible, radially-expandable, woven portion 305 and a single suture opening 306, as opposed to tube 16, which has a malecot anchoring structure and a plurality of suture openings 63-1, 63-2, 65-1 and 65-2. Tube 303 is shown with portion 305 in its axially-collapsed, radially-expanded, anchoring state in FIG. 17.

Assembly 301 may be implanted using the "over-the-wire" technique and, thereafter, may be used in the same way described above for assembly 11.

Figure 18A:
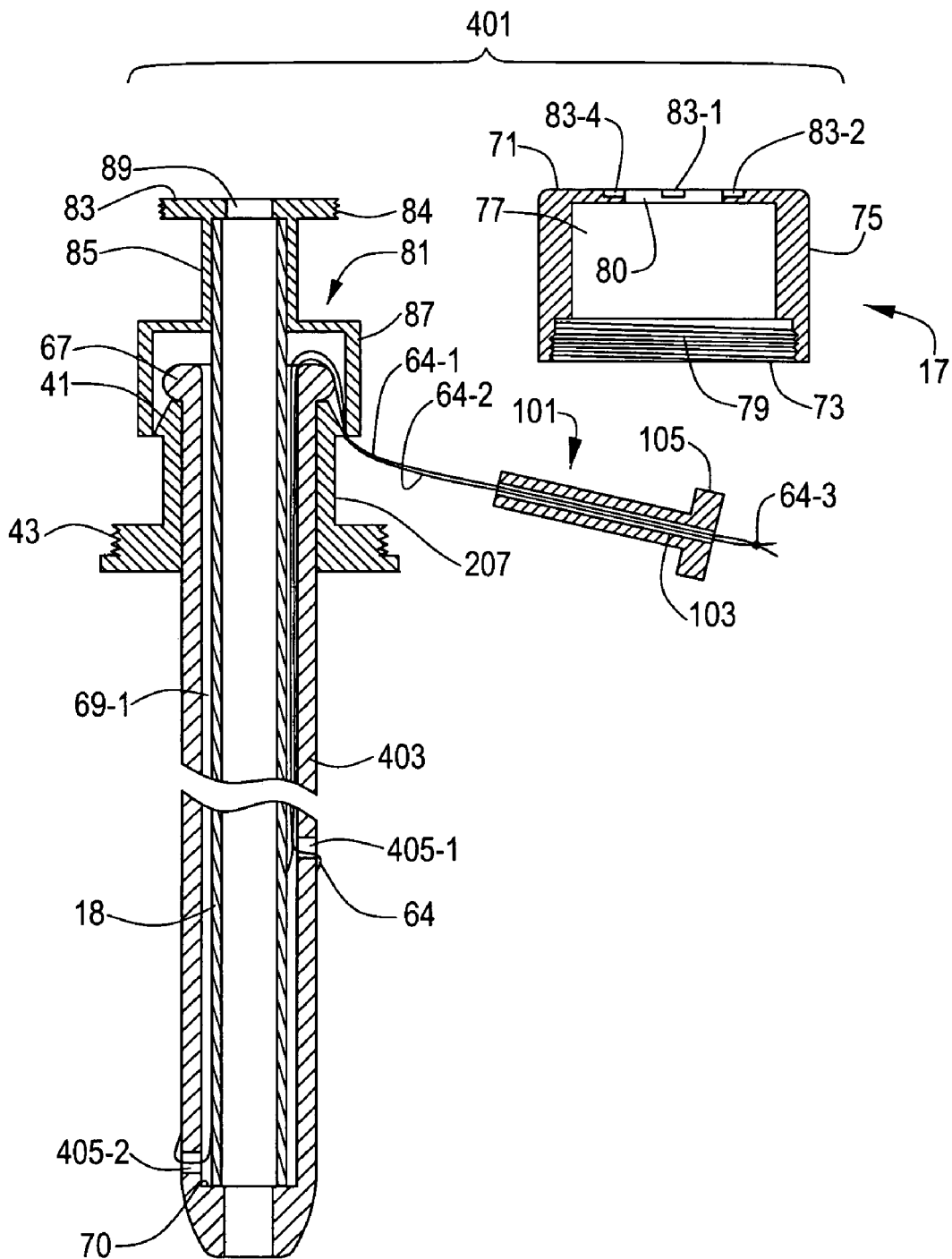
FIG. 18(a) is a partially exploded, fragmentary, section view of a fourth embodiment of a low profile medical catheter assembly constructed according to the teachings of the present invention.

Referring now to FIGS. 18(*a*) and 18(*b*), there are shown partially exploded, fragmentary, section and fragmentary front views, respectively, of a fourth embodiment of a low profile medical catheter assembly constructed according to the teachings of the present invention, said low profile medical catheter assembly being represented generally by reference numeral 401.

Assembly 401 is similar in many respects to assembly 201, the principal differences between the two assemblies being that (i) assembly 401 does not include base 205; and (ii) assembly 401 comprises a tube 403, instead of tube 216, tube 403 being a locking pigtail catheter having a pair of suture openings 405-1 and 405-2.

Assembly 401 may be implanted and used in the same way described above for assembly 201.

Figure 19:
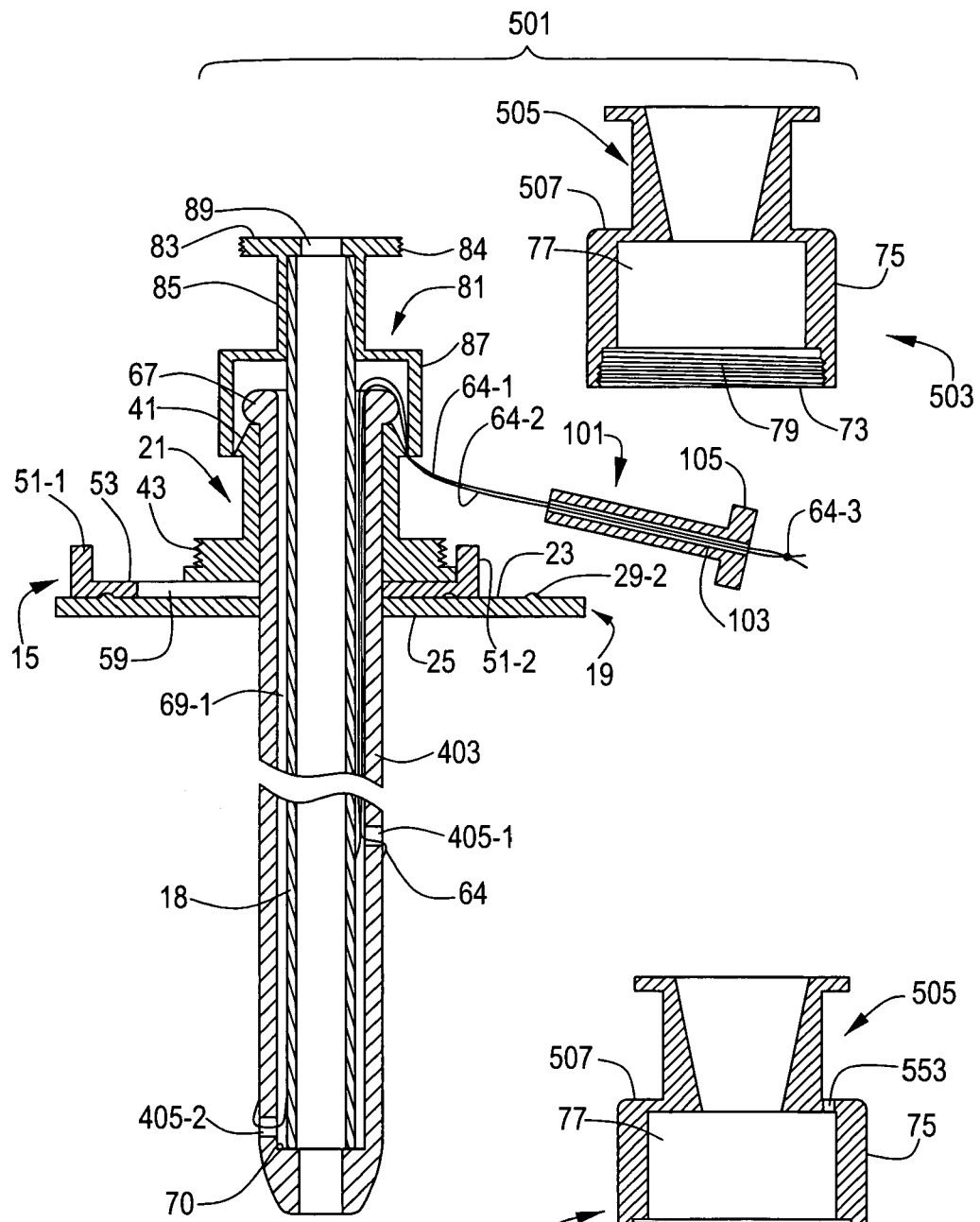
FIG. 19 is a partially exploded, fragmentary, section view of a fifth embodiment of a low profile medical catheter assembly constructed according to the teachings of the present invention.

Referring now to FIG. 19, there is shown a partially exploded, fragmentary, section view of a fifth embodiment of a low profile medical catheter assembly constructed according to the teachings of the present invention, said low profile medical catheter assembly being represented generally by reference numeral 501.

Assembly 501 is similar in many respects to assembly 301, the principal differences between the two assemblies being that (i) tube 303 of assembly 301 is replaced with tube 403 in assembly 501; and (ii) cap 17 of assembly 301 is replaced with cap 503 in assembly 501.

Cap 503 is similar to cap 17, the primary difference between the two caps being that cap 503 further includes a medical luer fitting 505 extending upwardly from top wall 507 and in fluid communication with cavity 77.

Figure 20:
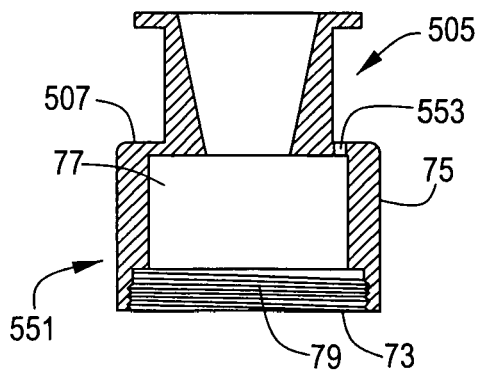
FIG. 20 is a section view of an alternative embodiment of a cap adapted for use with the low profile medical catheter assembly of FIG. 19.

Referring now to FIG. 20, there is shown a section view of an alternative cap 551 adapted for use with assembly 501, cap 551 differing from cap 503 only in that cap 551 further includes an opening 553 through which suture 64 may be passed (after being securely retained between top wall 507 and tube 403), instead of being passed through the open bottom end 73 of cap 503.

Assembly 501 may be implanted and, thereafter, used in the same way described above for assembly 301.

Figure 21:
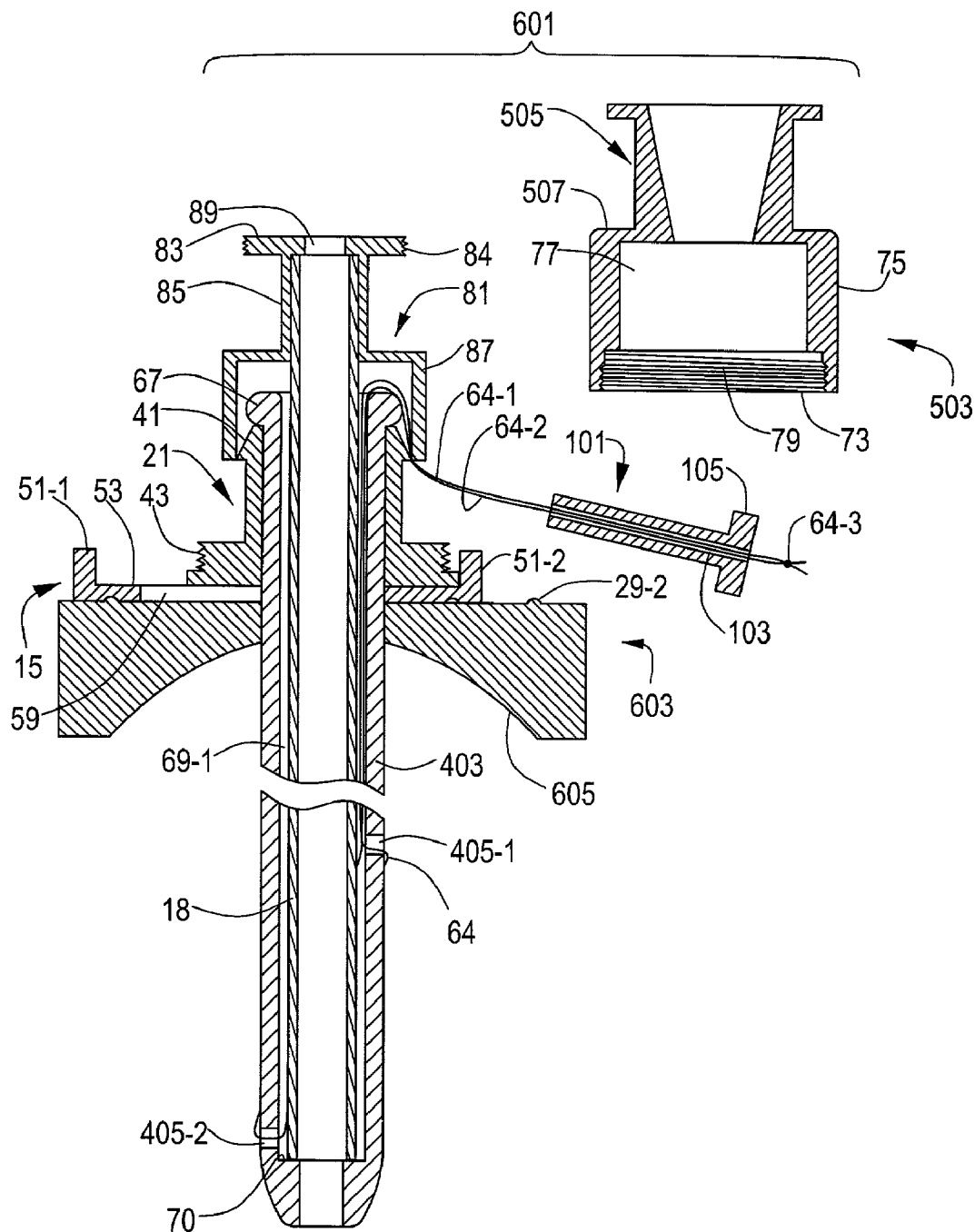
FIG. 21 is a partially exploded, fragmentary, section view of a sixth embodiment of a low profile medical catheter assembly constructed according to the teachings of the present invention.

Referring now to FIG. 21, there is shown a partially exploded, fragmentary, section view of a sixth embodiment of a low profile medical catheter assembly constructed according to the teachings of the present invention, said low profile medical catheter assembly being represented generally by reference numeral 601.

Figure 22:
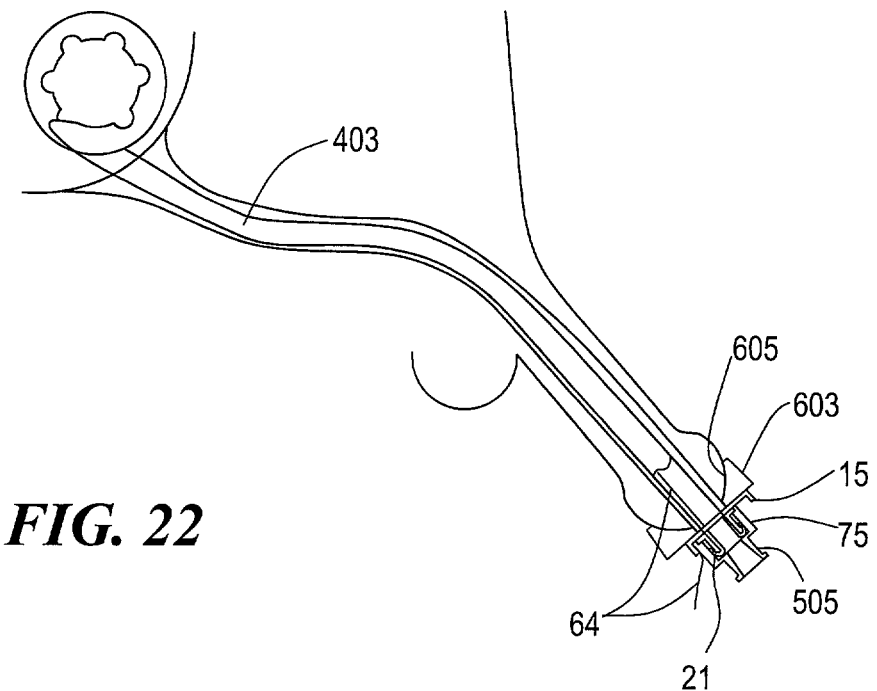
FIG. 22 is a schematic view, partly in section, showing the low profile medical catheter assembly of FIG. 21 implanted in a male patient for use in draining the bladder.

Assembly 601, which is a urethral catheter designed for use in draining the bladder of a male patient (but is not limited to said use), is similar in most respects to assembly 501, the principal difference between the two assemblies being that base 19 of assembly 501 is replaced with base 603 in assembly 601, the bottom of base 603 being shaped to include a concave surface 605 designed to conform closely to the shape of the tip of the patient's penis. FIG. 22 schematically shows assembly 601 deployed on a male patient. When urination is desired, clamp 15 is placed in its open position; otherwise, clamp 15 is placed in its closed position. As can be seen, because the assembly has a low profile, it can readily be concealed by the patient.

Figure 23:
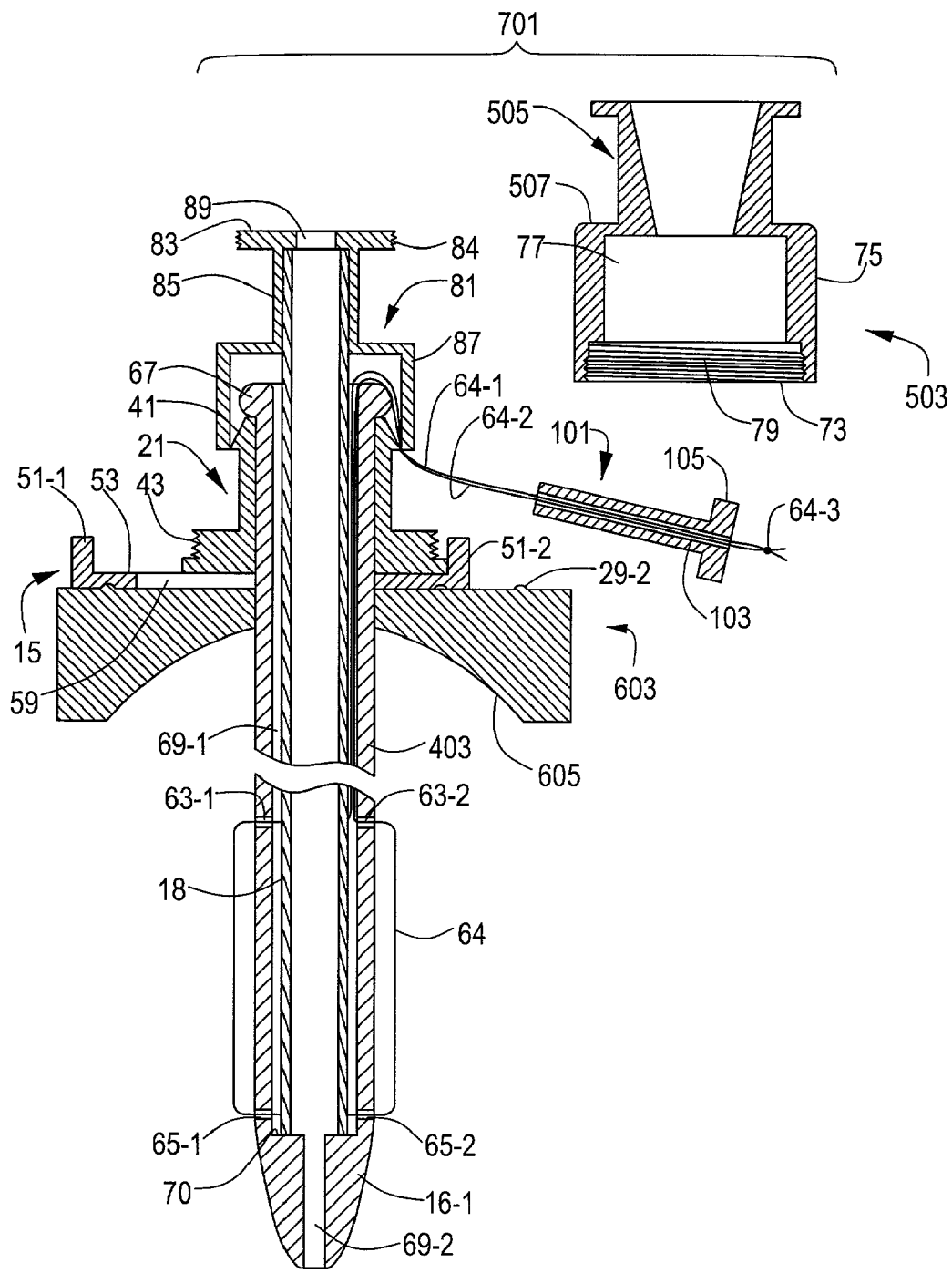
FIG. 23 is a partially exploded, fragmentary, section view of a seventh embodiment of a low profile medical catheter assembly constructed according to the teachings of the present invention.

Referring now to FIG. 23, there is shown a partially exploded, fragmentary, section view of a seventh embodiment of a low profile medical catheter assembly constructed according to the teachings of the present invention, said low profile medical catheter assembly being represented generally by reference numeral 701.

Figure 24:
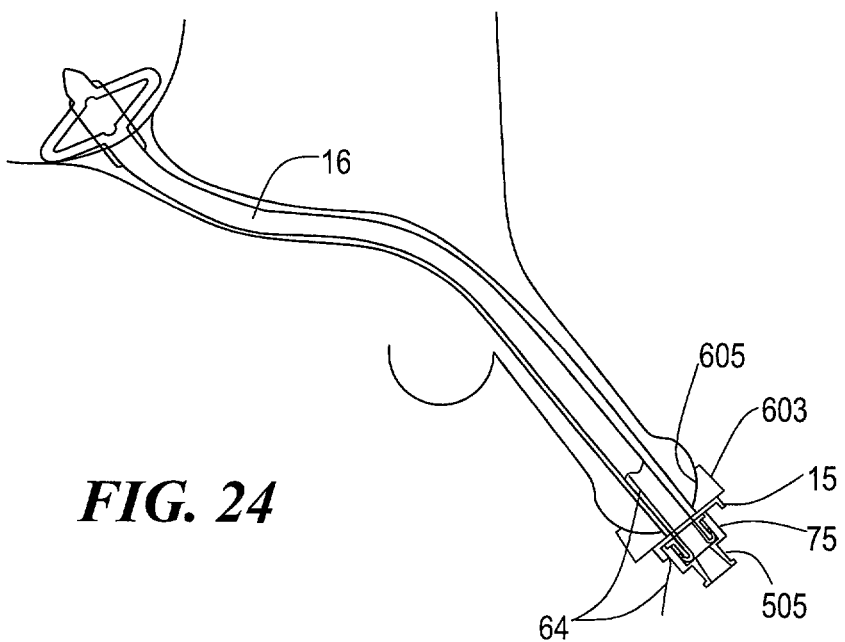
FIG. 24 is a schematic view, partly in section, showing the low profile medical catheter assembly of FIG. 23 implanted in a male patient for use in draining the bladder.

Assembly 701 is similar in most respects to assembly 601, the principal difference between the two assemblies being that tube 403 of assembly 601 is replaced with tube 16 in assembly 701. FIG. 24 schematically shows assembly 701 deployed on a male patient.

Figure 25:
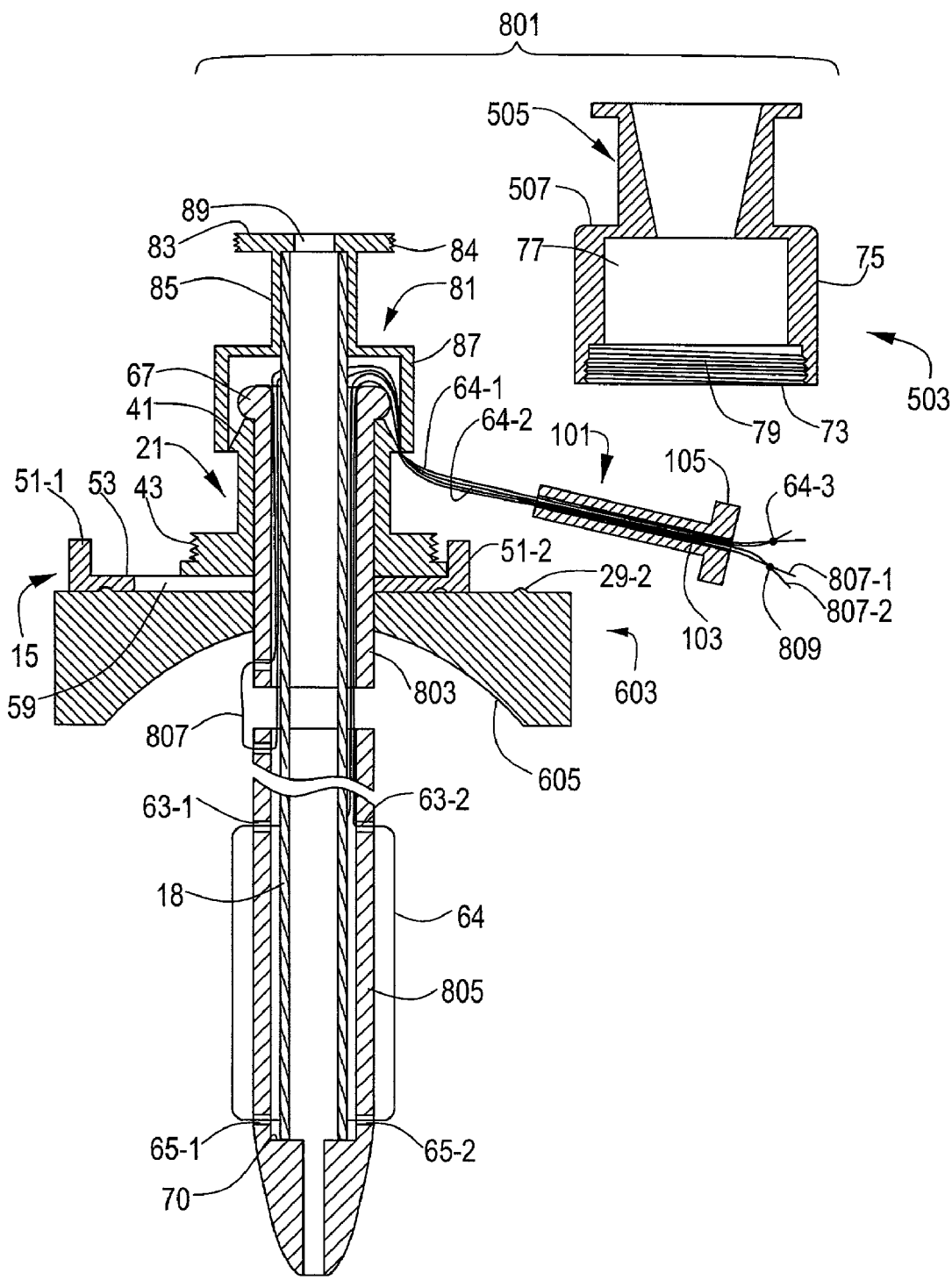
FIG. 25 is a partially exploded, fragmentary, section view of a eighth embodiment of a low profile medical catheter assembly constructed according to the teachings of the present invention.

Referring now to FIG. 25, there is shown a partially exploded, fragmentary, section view of an eighth embodiment of a low profile medical catheter assembly constructed according to the teachings of the present invention, said low profile medical catheter assembly being represented generally by reference numeral 801.

Figure 26:
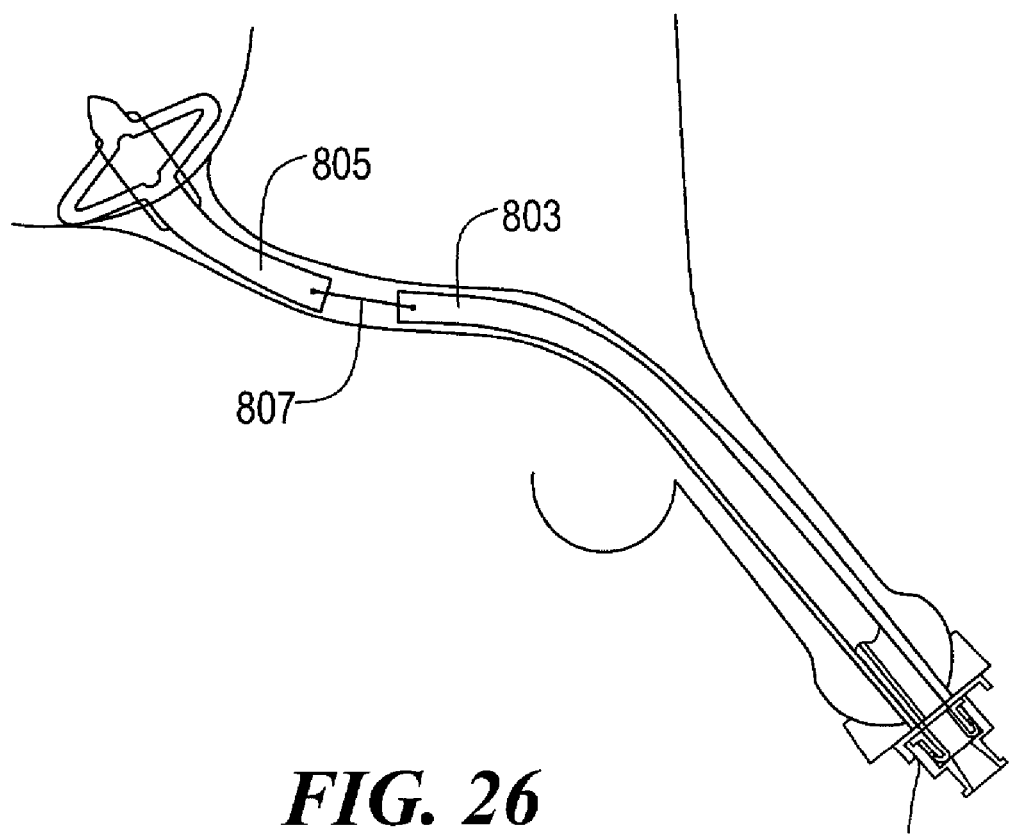
FIG. 26 is a schematic view, partly in section, showing the low profile medical catheter assembly of FIG. 25 implanted in a male patient for use in draining the bladder.

Assembly 801 is similar in most respects to assembly 701, the principal difference between the two assemblies being that tube 16 of assembly 701 is replaced with tube portions 803 and 805 in assembly 801, tube portion 803 corresponding generally to the proximal portion of tube 16 and tube portion 805 corresponding generally to the distal portion of tube 16. Tube portions 803 and 805 are coupled together by a looped suture 807, ends 807-1 and 807-2 of suture 807 being passed through sleeve 101 and tied together in a knot 809. As can readily be appreciated, the spacing of tube portions 803 and 805 can be varied by adjusting the loop size of suture 807. FIG. 26 schematically shows assembly 801 deployed on a male patient. As can be seen, assembly 801 is well-suited for longer term use as suture 807 provides minimal interference with the prostatic sphincter. In cases where penile reconstructive surgery has occurred, tube portions 803 and/or 805 can be shortened further to apply some tension along the length of the catheter.

The embodiments of the present invention described above are intended to be merely exemplary and those skilled in the art shall be able to make numerous variations and modifications to it without departing from the spirit of the present invention. For example, it is to be understood that other types of anchoring mechanisms, other than those disclosed, can be used and that other types of sutures and threads can also be used. All such variations and modifications are intended to be within the scope of the present invention as defined in the appended claims.

What is claimed is:

1. A medical catheter assembly comprising:
   (a) a medical catheter, said medical catheter having a proximal end, a distal end and a longitudinal bore, said distal end being shaped to include an internal bolster, said internal bolster having an anchoring state and a non-anchoring state;
   (b) a suture terminating in a pair of ends, said suture extending from said internal bolster through said longitudinal bore, with said ends of said suture exiting said medical catheter at said proximal end wherein proximal displacement of said suture maintains said internal bolster in said anchoring state; and
   (c) a protective sleeve made of a rigid material, said protective sleeve being removably insertable into said longitudinal bore of said medical catheter through said proximal end, said suture being inserted through said protective sleeve, with said ends of said suture extending proximally beyond said protective sleeve, and wherein the ends are capable of being knotted.

2. The medical catheter assembly as claimed in claim 1 further comprising a body adapted for use as an external bolster, said medical catheter extending through said body.

3. The medical catheter assembly as claimed in claim 2 wherein said body comprises a sleeve through which said medical catheter extends, said sleeve extending upwardly and having a longitudinal bore.

4. The medical catheter assembly as claimed in claim 3 further comprising a cap, said cap being removably mountable on said sleeve.

5. The medical catheter assembly as claimed in claim 4 wherein said cap has an opening, said opening being alignable with said longitudinal bore of said sleeve.

6. The medical catheter assembly as claimed in claim 5 wherein said cap further has a medical luer fitting, said medical luer fitting being in fluid communication with said opening.

7. The medical catheter assembly as claimed in claim 2 wherein said body comprises a base and a sleeve, said base having a transverse bore, said sleeve extending upwardly from said base and having a longitudinal bore, said longitudinal bore of said sleeve being aligned with said transverse bore of said base, said medical catheter extending through said transverse bore of said base and said longitudinal bore of said sleeve.

8. The medical catheter assembly as claimed in claim 7 wherein the bottom of said base has a concave surface.

9. The medical catheter assembly as claimed in claim 7 wherein said sleeve is shaped to include an external barb over which said proximal end of said medical catheter may be inverted.

10. The medical catheter assembly as claimed in claim 1 further comprising a cannula, said cannula being removably disposed within said longitudinal bore of said medical catheter for maintaining said medical catheter in said non-anchoring state.

11. The medical catheter assembly as claimed in claim 10 wherein said cannula has a proximal end and a distal end, said medical catheter assembly further comprising a cannula hub, said cannula being fixed at its proximal end to said cannula hub.

12. The medical catheter assembly as claimed in claim 11 further comprising a trocar and a trocar hub, said trocar having a proximal end and distal end, said proximal end of said trocar being fixed to said trocar hub, said trocar being removably inserted into said cannula and said medical catheter in such a way as to extend therethrough, said trocar hub being removably mounted on said cannula hub.

13. The medical catheter assembly as claimed in claim 12 further comprising a body adapted for use as an external bolster, said medical catheter extending through said body, said cannula hub being removably mounted on said body.

14. The medical catheter assembly as claimed in claim 11 further comprising a body adapted for use as an external bolster, said medical catheter extending through said body, said cannula hub being removably mounted on said body.

15. The medical catheter assembly as claimed in claim 1 wherein said internal bolster is a pigtail bolster.

16. The medical catheter assembly as claimed in claim 1 wherein said internal bolster has a malecot structure.

17. The medical catheter assembly as claimed in claim 1 wherein said internal bolster is an axially-collapsible, radially-expandable, mesh bolster.

18. The medical catheter assembly as claimed in claim 1 wherein said proximal end of said medical catheter is shaped to include an external flange.

19. The medical catheter assembly as claimed in claim 1 further comprising a trocar, said trocar being removably inserted into said medical catheter in such a way as to extend therethrough.

20. The medical catheter assembly as claimed in claim 1 wherein said protective sleeve has a proximal end and a distal end, said proximal end being shaped to include a flange adapted to rest upon the proximal end of said medical catheter.

21. A medical catheter assembly comprising:
   (a) a medical catheter, said medical catheter having a proximal end, a distal end and a longitudinal bore, said distal end being shaped to include an internal bolster, said internal bolster having an anchoring state and a non-anchoring state;
   (b) a suture having a pair of ends, said suture extending from said internal bolster through said longitudinal bore, with said ends of said suture exiting said medical catheter at said proximal end wherein proximal displacement of said suture maintains said internal bolster in said anchoring state;
(c) a protective sleeve made of a rigid material, said protective sleeve being removably insertable into said longitudinal bore of said medical catheter through said proximal end, said suture being inserted through said protective sleeve, with said ends of said suture extending proximally beyond said protective sleeve;
(d) a body adapted for use as an external bolster, said medical catheter extending through said body, said body comprising a sleeve through which said medical catheter extends, said sleeve extending upwardly and having a longitudinal bore and an external thread; and
(e) a cap, said cap being removably mountable on said sleeve, said cap having an internal thread whereby said cap is adapted to be removably screwed onto said sleeve by threaded engagement of said internal thread with said external thread.

22. The medical catheter assembly as claimed in claim 21 wherein said cap further has one or more recesses adapted to receive a tool for screwing said cap onto said sleeve and for unscrewing said cap from said sleeve.

23. A medical catheter assembly comprising:
(a) a medical catheter, said medical catheter having a proximal end, a distal end and a longitudinal bore, said distal end being shaped to include an internal bolster, said internal bolster having an anchoring state and a non-anchoring state;
(b) a suture extending from said internal bolster through said longitudinal bore to exit said medical catheter at said proximal end wherein proximal displacement of said suture maintains said internal bolster in said anchoring state;
(c) a protective sleeve made of a rigid material, said protective sleeve being removably insertable into said medical catheter through said proximal end, said suture being inserted through said protective sleeve;
(d) a body adapted for use as an external bolster, said medical catheter extending through said body, said body comprising a base and a sleeve, said base having a transverse bore, said sleeve extending upwardly from said base and having a longitudinal bore, said longitudinal bore of said sleeve being aligned with said transverse bore of said base, said medical catheter extending through said transverse bore of said base and said longitudinal bore of said sleeve, said sleeve further being shaped to include an external barb over which said proximal end of said medical catheter may be inverted, said sleeve further comprising a transverse slot, said transverse slot intersecting said longitudinal bore; and
(e) a clamp movable within said transverse slot between a first position in which said clamp compresses to closure the medical catheter and a second position in which said clamp does not compress the medical catheter.

24. A medical catheter assembly comprising:
(a) a medical catheter, said medical catheter having a proximal end, a distal end and a longitudinal bore, said distal end being shaped to include an internal bolster, said internal bolster having an anchoring state and a non-anchoring state;
(b) a suture extending from said internal bolster through said longitudinal bore to exit said medical catheter at said proximal end wherein proximal displacement of said suture maintains said internal bolster in said anchoring state;
(c) a protective sleeve made of a rigid material, said protective sleeve being removably insertable into said medical catheter through said proximal end, said suture being inserted through said protective sleeve;
(d) a body adapted for use as an external bolster, said medical catheter extending through said body, said body comprising a base and a sleeve, said base having a transverse bore, said sleeve extending upwardly from said base and having a longitudinal bore, said longitudinal bore of said sleeve being aligned with said transverse bore of said base, said medical catheter extending through said transverse bore of said base and said longitudinal bore of said sleeve, said sleeve further being shaped to include an external barb over which said proximal end of said medical catheter may be inverted, said sleeve further comprising a transverse slot, said transverse slot intersecting said longitudinal bore;
(e) a clamp movable within said transverse slot between a first position in which said clamp compresses to closure the medical catheter and a second position in which said clamp does not compress the medical catheter;
(f) a cannula, said cannula having a proximal end and a distal end and being removably positionable within said longitudinal bore of said medical catheter to cause said medical catheter to change between said anchoring state and said non-anchoring state;
(g) a cannula hub, said cannula hub being fixed to said proximal end of said cannula;
(h) a cap;
(i) wherein said cap and said cannula hub are alternatively removably mountable on said body;
(j) a trocar, said trocar having a proximal end and a distal end and being removably insertable into said medical catheter in such a way as to extend therethrough; and
(k) a trocar hub, said trocar hub being fixed to said proximal end of said trocar and being removably mountable on said cannula hub.

25. A medical catheter assembly comprising:
(a) a medical catheter, said medical catheter having a proximal end, a distal end and a longitudinal bore, said distal end being shaped to include an internal bolster, said internal bolster having an anchoring state and a non-anchoring state;
(b) a suture terminating in a pair of ends, said suture extending from said internal bolster through said longitudinal bore, with said ends of said suture exiting said medical catheter at said proximal end wherein proximal displacement of said suture maintains said internal bolster in said anchoring state; and
(c) a protective sleeve made of a rigid material, said protective sleeve having a proximal end and a distal end, said distal end of said protective sleeve being removably insertable into said medical catheter through said proximal end, said ends of said suture extending through and proximally beyond said protective sleeve, said protective sleeve being movable distally relative to said ends of said suture, and wherein the ends are capable of being knotted.

* * * * *